(12) United States Patent
Helfrich et al.

(10) Patent No.: US 11,732,282 B2
(45) Date of Patent: Aug. 22, 2023

(54) PROCESS FOR THE PURIFICATION OF L-FUCOSE FROM A FERMENTATION BROTH

(71) Applicant: Chr. Hansen HMO GmbH, Rheinbreitbach (DE)

(72) Inventors: Markus Helfrich, Bad Hoenningen (DE); Stefan Jennewein, Bad Honnef (DE)

(73) Assignee: Chr. Hansen HMO GmbH, Rheinbreitbach (DE)

( * ) Notice: Subject to any disclaimer, the term of this patent is extended or adjusted under 35 U.S.C. 154(b) by 338 days.

(21) Appl. No.: 16/765,833

(22) PCT Filed: Nov. 15, 2018

(86) PCT No.: PCT/EP2018/081468
§ 371 (c)(1),
(2) Date: May 20, 2020

(87) PCT Pub. No.: WO2019/101629
PCT Pub. Date: May 31, 2019

(65) Prior Publication Data
US 2020/0354760 A1 Nov. 12, 2020

(30) Foreign Application Priority Data
Nov. 21, 2017 (EP) .................................... 17202833
Oct. 31, 2018 (WO) ................. PCT/EP2018/079908

(51) Int. Cl.
| | |
|---|---|
| *C12P 19/02* | (2006.01) |
| *A23L 33/125* | (2016.01) |
| *A23L 33/00* | (2016.01) |
| *A61K 31/7012* | (2006.01) |
| *C12P 19/26* | (2006.01) |
| *C07H 1/08* | (2006.01) |
| *C07H 3/08* | (2006.01) |
| *C07H 1/06* | (2006.01) |
| *C07H 7/027* | (2006.01) |

(52) U.S. Cl.
CPC ............ *C12P 19/02* (2013.01); *A23L 33/125* (2016.08); *A23L 33/40* (2016.08); *A61K 31/7012* (2013.01); *C07H 1/06* (2013.01); *C07H 1/08* (2013.01); *C07H 3/08* (2013.01); *C07H 7/027* (2013.01); *C12P 19/26* (2013.01)

(58) Field of Classification Search
None
See application file for complete search history.

(56) References Cited

U.S. PATENT DOCUMENTS

| | | | |
|---|---|---|---|
| 3,240,775 A | 3/1966 | Schweiger | |
| 3,240,776 A | 3/1966 | Miller | |
| 8,642,297 B2 | 2/2014 | Wymer et al. | |
| 10,377,787 B2 * | 8/2019 | Jennewein | A23L 29/30 |
| 10,882,880 B2 * | 1/2021 | Jennewein | C07H 1/08 |
| 2010/0113390 A1 | 5/2010 | Fujikawa et al. | |
| 2011/0129938 A1 | 6/2011 | Kobayashi et al. | |
| 2011/0300584 A1 | 12/2011 | Hüfner et al. | |
| 2012/0135467 A1 | 5/2012 | Jennewein et al. | |
| 2013/0007267 A1 | 1/2013 | Khatutsky | |
| 2014/0024820 A1 | 1/2014 | Parkot et al. | |
| 2014/0120611 A1 | 5/2014 | Jennewein et al. | |
| 2015/0240277 A1 | 8/2015 | Jennewein et al. | |
| 2016/0333042 A1 * | 11/2016 | Jennewein | A61P 1/00 |
| 2018/0273996 A1 | 9/2018 | Jennewein et al. | |
| 2019/0382737 A1 | 12/2019 | Hüfner et al. | |
| 2020/0032308 A1 | 1/2020 | Jennewein et al. | |

FOREIGN PATENT DOCUMENTS

| | | | | |
|---|---|---|---|---|
| CN | 104628794 A | 5/2015 | | |
| EP | 0102535 A2 | 3/1984 | | |
| EP | 0474410 A2 | 3/1992 | | |
| EP | 2258216 A1 | 12/2010 | | |
| EP | 2479263 B1 * | 11/2013 | ............... | C07H 3/04 |
| JP | S6327496 A | 2/1988 | | |
| JP | H08119986 A | 5/1996 | | |
| JP | H1135591 A | 2/1999 | | |
| JP | 2000351790 A | 12/2000 | | |
| JP | 2017506065 A | 3/2017 | | |
| RU | 2524425 C2 | 7/2014 | | |
| RU | 2571274 C2 | 12/2015 | | |
| WO | 9715683 A1 | 5/1997 | | |
| WO | 03041512 A1 | 5/2003 | | |

(Continued)

OTHER PUBLICATIONS

Saufi et al. J Chromatogr A. Dec. 16, 2011;1218(50):9003-9 (Year: 2011).*
Sarney et al. Biotechnol Bioeng. Aug. 20, 2000;69(4):461-7 (Year: 2000).*
International Search Report for PCT/EP2018/081468 dated Feb. 11, 2019.
Hans-Peter Hauber, et al., "Inhalation with fucose and galactose for treatment of Pseudomonas aeruginosa in cystic fibrosis patients," International journal of medical sciences, (2008), vol. 5, No. 6:371-376.
L. Robert, et al., "Effect of L-fucose and fucose-rich polysaccharides on elastin biosynthesis, in vivo and in vitro," Biomedicine & pharmacotherapy, (2004), vol. 58, No. 2:123-128.

(Continued)

*Primary Examiner* — Christian L Fronda
(74) *Attorney, Agent, or Firm* — McNeill Baur PLLC

(57) ABSTRACT

The present invention concerns an efficient way to isolate L-fucose from a fermentation broth. The L-fucose contained in the fermentation broth is produced by microbial fermentation (bacterial or yeasts). The inventive process comprises a step of removing biomass from the fermentation broth, a step of subjecting the resulting solution to at least one of a cationic ion exchanger treatment and an anionic ion exchanger treatment and a step of removing salts after the ion exchanger treatment. The process can provide L-fucose in powder form, in granulated form as well as in form of L-fucose crystals.

33 Claims, 7 Drawing Sheets

(56) References Cited

FOREIGN PATENT DOCUMENTS

| | | |
|---|---|---|
| WO | 2005040430 A1 | 5/2005 |
| WO | 2005087941 A1 | 9/2005 |
| WO | 2008040717 A2 | 4/2008 |
| WO | 2008090631 A1 | 7/2008 |
| WO | 2010070104 A1 | 6/2010 |
| WO | 2010142305 A1 | 12/2010 |
| WO | 2012034996 A1 | 3/2012 |
| WO | 2012049257 A1 | 4/2012 |
| WO | 2012097950 A1 | 7/2012 |
| WO | 2012112777 A2 | 8/2012 |
| WO | 2014067696 A1 | 5/2014 |
| WO | 2015032412 A1 | 3/2015 |
| WO | 2015071401 A1 | 5/2015 |
| WO | 2015071403 A1 | 5/2015 |
| WO | 2015106943 A1 | 7/2015 |
| WO | 2016091265 A1 | 6/2016 |
| WO | 2016120448 A1 | 8/2016 |
| WO | 2016150629 A1 | 9/2016 |

OTHER PUBLICATIONS

Taku Chiba and Tejima Setsuzo, "A new synthesis of α-L-fucose," Chemical and Pharmaceutical Bulletin, (1979), vol. 27, No. 11:2838-2840.

Chi-Huey Wong, et al., "Enzymic synthesis of L-fucose and analogs," The Journal of Organic Chemistry, (1995), vol. 30, No. 22:7360-7363.

Florian Baumgärtner, et al., "Construction of *Escherichia coli* strains with chromosomally integrated expression cassettes for the synthesis of 2'-fucosyllactose," Microbial cell factories, (2013), vol. 12, No. 40.

Machine translation of RU 2571274, Korneeva et al., Dec. 20, 2015, 5 pages.

* cited by examiner

PROCESS FOR THE PURIFICATION OF L-FUCOSE FROM A FERMENTATION BROTH

CROSS-REFERENCE TO RELATED APPLICATIONS

This application is the National Stage entry of International Application No. PCT/EP2018/081468, filed 15 Nov. 2018, which claims priority to International Application No. PCT/EP2018/079908, filed 31 Oct. 2018, and European Patent Application No. 17202833.4, filed 21 Nov. 2017.

BACKGROUND

Field

The present invention concerns an efficient way to isolate L-fucose from a fermentation broth. The L-fucose contained in the fermentation broth is produced by microbial fermentation (bacterial or yeasts). The inventive process comprises a step of removing biomass from the fermentation broth, a step of subjecting the resulting solution to at least one of a cationic ion exchanger treatment and an anionic ion exchanger treatment and a step of removing salts after the ion exchanger treatment. The process can provide L-fucose in powder form, in granulated form as well as in form of L-fucose crystals.

DESCRIPTION OF RELATED ART

Carbohydrates play roles in all forms of life by taking on vital roles in energy storage, structural function, signalling, information storage etc. For this task, nature synthesizes several major monosaccharides like glucose, N-acetylglucosamine, mannose, N-acetyl-mannosamine, fructose, fucose, ribose, L-fucose, xylose etc. and several minor ones for more specialized applications, like for example D-allose.

L-fucose (6-deoxy-L-galactose) is one of the so-called rare monosaccharides. It is found in many of natural products in both D- and L-form: L-fucose (also called isodulite) and D-fucose (CAS 3615-37-0). The L-shape is the most common in nature. L-fucose is an elementary molecule for use in research and development and a characteristic component of glycan structures. Scientific investigations in the field of fucosylated substances have shown, among other things that they have an outstanding importance in embryonic development and are involved in the immune response of the organism.

L-fucose and fucosylated oligo- and polysaccharides are of great interest for the chemical, food, cosmetic and pharmaceutical industry since they have high potential for nutritional and biomedical applications (Hauber et al., 2008, Int. J. Med. Sci. 5:371-376.; Isnard et al., 2005, Ophthalmologics 219:324-333; Robert et al., 2004, Biomed. Pharmacother. 58:123-128; Wild et al., 2002, Cells Tissues Organs 172: 161-173; Adam et al., 1997, Am. J. Respir. Care Med. 155:2102-2104). In addition, fucosylated derivatives are known for their antiallergic and emulsifying properties. It is also known that L-fucose supplied by the food can be used for the synthesis of fucosylated glycans via the L-fucose salvage pathway present in mammals. Thus, L-fucose is important for the development of the brain and the immune system. The importance is also evidenced by leukocyte adhesion deficiency II syndrome, an inherited disorder of fucose metabolism.

In mammalian cells, L-fucose is present in fucosylated glycans such as the ABO blood group antigens and human milk oligosaccharides. L-fucose and fucosylated oligosaccharides or proteins are also of great interest in the chemical, pharmaceutical and nutraceutical industry.

L-fucose is also found in human breast milk at a concentration of approximately (0.5 g/l), among others. Human breast milk is given an important role in healthy child development. The substances occurring therein, in particular the oligosaccharides (human milk oligosaccharides (HMO)) are one of the main solid components of breast milk and have a core structure which has a lactose unit at the reducing end and is branched or chain-continued with N-acetyllactosamine. The structural variability is extended by fucosyl modifications at the end positions. In terms of health and developmental benefits, the biological function of HMOs has been the subject of numerous studies, but requires the technical purification of the compounds in sufficient quantities. In the prior art, it is known to provide L-fucose either by direct extraction from natural sources or by chemical modification of monosaccharides (P T Vanhooren et al., 1999, J. Chem., Technol., Biotechnol., 74, 479).

While some monosaccharides can be obtained from nature in large amounts and at reasonable cost (e.g. glucose, N-acetylglucosamine and fructose), most monosaccharides are rather scarce and can be found in nature only in small amounts, like for example L-fucose (6-deoxy-L-galactose).

For commercial production of monosaccharides, almost exclusively oligosaccharides obtained from nature are used as sources. These oligosaccharides are acid-hydrolysed and from the released monosaccharides the individual sugars are purified. Due to the high chemical similarity of the monosaccharides (mostly differing from each other only by the orientation of individual hydroxyl-groups) the separation of individual monosaccharides in pure form is rather laborious and costly.

Natural sources of L-fucose are polysaccharides from plants such as seeweed (Fucoidan, sulphated fucose polymer), potatoes, soybeans etc. In plants, fucose is typically associated with polysaccharides which having Lfucopyranosyl units at the ends of or within the polysaccharide chain. Another important occurrence of L-fucose is in extracellular polysaccharides from bacteria, fungi and microalgae.

L-fucose can obtain from natural sources, such as algae or bacterial origins by various extraction methods. These rare materials of natural origin used in the recovery of L-fucose are typically multicomponent mixtures. L-fucose is currently obtained via the hydrolysis of these complex oligosaccharides. The separation of L-fucose with a sufficient purity is difficult to achieve and is a problem in the state of the art.

For the purification of individual monosaccharides from complex hydrolysates, often noxious chemical have to be employed. For example, U.S. Pat. No. 3,240,776 discloses an extraction method for L-fucose in which L-fucose is isolated by using lead acetate and excessive amounts of organic solvents.

Therefore, the isolation of individual monosaccharides from a complex hydrolysate of oligosaccharides is challenging (due to the high chemical similarity of the individual monosaccharides released) and environmentally harmful (due to the excessive use of toxic chemicals, such a lead carbonate). Also, the availability of oligosaccharides rich in a certain sugar can be rather restricted in nature and also highly variable due to seasonal changes. L-fucose is mainly derived from the polysaccharide fucoidan, a fucan monosulfate present in all common brown seaweeds comprising the families Fucaceae and Laminariaceae (Black, W. A. P (1954): The seasonal variation in the combined L-fucose content of the common british Laminariaceae and Fucaceae. J. Sci. Food Agric. 5, 445-448).

Today, L-fucose is obtained in large quantities mainly by the collection of brown seaweed belonging to the family Fucaceae, which can be found worldwide but in high amounts at the European shores of the Atlantic Ocean. The large-scale harvest of brown seaweed from sea shores causes environmental concerns and is limited by environmental protection laws. L-fucose and L-fucose-containing substances are the subject of ongoing research.

For example, JP 2000351790 discloses a method for extracting fucoidan and for obtaining and separating a fucose-containing oligosaccharide from the extracted fucoidan.

WO 2012/034996 A1 shows that L-fucose can also be obtained via the hydrolysis of natural occurring L-fucose containing bacterial polysaccharides. This document discloses a strain belonging to the Enterobacteriaceae family, which strain is able to produce extracellular polysaccharides which contain L-fucose. For the production of L-fucose, the polysaccharides produced by the strain are recovered and subjected to hydrolysis, e.g. by treatment with sulphuric acid or trifluoroacetic acid.

Besides the extraction of L-fucose from poly- or oligosaccharide hydrolysates, different methods for synthetic production of L-fucose have been developed. This production processes start from other monosaccharides, like L-arabinose, D-galactose, L-rhamnose, D-mannose and D-glucose. With the most efficient synthetic route starting from the rare monosaccharide L-rhamnose, an efficient synthesis of L-fucose could be reached (Defaye et al., 1984, Carbohydr. Res. 126, 165-169). Generally, the yields of these chemical syntheses are often rather poor and involve several chemical steps. Besides involving several synthetic steps, extensive protection group chemistry has to be used for the chemical synthesis of L-fucose. In general, the large-scale chemical synthesis of monosaccharides has not proven to be economically viable in comparison to extraction of L-fucose from polysaccharides collected from nature.

Recovery of the L-fucose has typically required sophisticated separation techniques such as chromatography with anion or cation exchange resins, dialysis, fractional crystallization, etc., depending on the nature of the accompanying sugars or sugar-related compounds (WO 2005/040430 A1).

JP 63 027496 describes direct extraction of L-fucose from algae belonging to the family of the Chordariaceae or Spermatochnaceae. The algae were dispersed in water and treated with concentrated sulfuric acid. The obtained hydrolysed algae solution was cooled and the insoluble substances were removed by filtration. The pH of the filtrate was adjusted to 5, the filtrate was treated with charcoal and filtered. In order to digest and remove other sugars than L-fucose, a yeast was added to the filtrate. The mixture was treated with charcoal and filtered. The filtrate was treated with cationic and anionic exchange resins for deionization and concentrated. The concentrated sugar solution was mixed with ethanol and allowed to crystallize. In this way, L-fucose with a purity of 98.7% was obtained.

One publication describes the isolation of pectins from an ethanol-insoluble residue of sugar beet pulp (Rombouts et al., 1986, Carbohydrate Research, 154:177-187). The isolated pectins were purified by chromatography on DEAE-cellulose or by precipitation with $CuSO_4$. The pectins had relatively high contents of neutral sugars. The main neutral sugars in each pectin were arabinose and galactose; other sugars present were rhamnose, L-fucose, xylose, mannose and glucose. L-fucose was not separated from the sugar/pectin mixture.

Thus, at present, the preparation of any monosaccharide in pure form requires a significant effort in the separation of the desired monosaccharide from other monosaccharides in a mixture, often involving large volumes of organic solvents and other noxious chemicals. As a consequence, the exclusive accumulation of a single desired monosaccharide, like for example L-fucose, would be of immense help. However, most microorganisms are restricted in the kinds of monosaccharides they are able to utilize. In addition, they often exert strong preferences towards certain monosaccharides in case that several monosaccharides are available at the same time as carbon source.

Another possible way for production of L-fucose is chemical synthesis. Deoxygenation of the C-6 carbon of D-galactose results in D-fucose. However, this methodology is not practical for the synthesis of L-fucose as L-galactose is not available in large quantities. L-fucose is obtainable from L-arabinose via a complex reaction sequence involving numerous intermediates. Inversion of configuration at C-5 and deoxygenation of C-6 in D-glucose provides L-fucose in a multistep procedure.

L-fucose can also be obtained via chemical synthesis from L-arabinose (Tanimura, 1961, Chem. Abstr. 55:12306), from D-glucose (Chiba, T. & Tejima, 1979, Chem. Pharm. Bull. 27:2838-2840), from methyl-L-rhamnose (Defaye, J., et al., 1984, Carbohydrate Res. 126:165-169), from D-mannose (Gesson, J-P et al., 1992, Tetrahedron Lett. 33:3637-3640) and from D-galactose (DejterJuszynski, M & Flowers, H-M., 1973, Carbohydrate Res. 28:144-146). Enzymatic syntheses of L-fucose and its analogues have been carried out from fuculose-6-phosphate using a multi-enzymatic system (see WO 97/15683 A1).

Starting from D-mannose, a stereoselective chain elongation on C-1 and cleavage of the terminal glycol portion are needed to produce L-fucose. L-rhamnose as a 6-deoxy hexose requires OH-inversions, namely at C-2 and C-4 to yield L-fucose. D-galactose has seemed to be the most suitable starting material for producing L-fucose as there is no need to perform inversion: reduction of the C-1 formyl group and oxidation of the C-6 primary hydroxyl to formyl provides L-fucose. The common characteristic of the above-mentioned processes is the unavoidable temporary protection of the hydroxyls that are not to undergo the configurational inversion, deoxygenation, and reduction and/or oxidation steps of the process. The numerous protection/deprotection steps, frequently requiring selective techniques, make these methodologies ineffective. In addition, in some cases laborious chromatographic separations are required to isolate intermediates from by-products.

WO 2014/067696 A1 describes for the first time a process for production of L-fucose by using a recombinant microorganism that possesses a glycosyltransferase and a glycosidase which work together to synthesize L-fucose in a free form. This process needs two enzymes and an acceptor molecule. The glycosyltransferase catalyses the transfer of fucose from GDP-L-fucose to the acceptor, for example lactulose, to synthesize fucosyllactulose. The fucosylated acceptor (e.g. Fucosyllactulose) is then hydrolysed by a glycosidase into the acceptor molecule and L-fucose. The acceptor is then again available for fucosylation by the employed fucosyltransferase. L-fucose is then liberated from the cell by export into the medium where it can be retrieved from the supernatant. By this means, the feedback inhibition of the GDP-fucose pathway can be easily overcome and significant (several g/l) amounts of free L-fucose can be obtained by microbial fermentation.

L-fucose itself and fucosylated substrates are important starting materials in the chemical and pharmaceutical industries as well as useful in the manufacture of cosmetics and nutraceuticals. Therefore, there is a constant need for innovative production processes for the production of L-fucose on an industrial scale.

Biotechnological methods have been proposed to recover L-fucose. For example, WO 2012/034996 A1 teaches a process for the production of L-fucose using an isolated microorganism of the family Enterobacteriaceae for the fermentative production of L-fucose. However, the L-fucose is obtained only after time-consuming fermentation as a non-purified mixture, so elaborate further purification steps are required to obtain L-fucose.

U.S. Pat. No. 8,642,297 B2 postulates a generic fermentative process intended for the production of L-fucose using a recombinant *Apium graveolens* mannitol-1-dehydrogenase. However, neither a concrete embodiment nor an example is disclosed for this purpose. Furthermore, no alternative enzyme is disclosed which could be used for the reaction.

WO 2005/087941 A1 discloses a combined fermentative-enzymatic process for the production of L-fucose. In this case, L-fuculose is first produced from L-fucitol by using a dehydrogenase of an acetobacterium. This must then be synthesized in a further step to L-fucose.

Another method describes the separation of complex mixtures of oligosaccharides by anion-exchange chromatography (Derevitskaya et al., 1975, Dokl. Akad. Nauk. SSSR, 223:1137-1139). In accordance with the disclosure, 2-amino-2-deoxyglucitol, glucosamine, galactose and L-fucose were successfully separated from oligosaccharide mixtures, buffered by 0.2 M borate, by anion-exchange chromatography.

JP H11-035591 discloses a process to produce L-fucose from fucoidan prepared from *Cladosiphon okamuranus Tokida* or an extract containing fucoidan. The process is a multistep process comprising for example treatments with water and/or an acid, neutralization, dialysis and electrodialytic treatments and ion exchange treatment using alkali as the eluent. L-fucose is finally crystallized from an alcohol.

Enzymatic and microbial synthesis has also been used for the production of L-fucose. L-fucose is produced by enzymatic synthesis from dihydroxyacetone phosphate (DHAP) and DL-lactaldehyde catalyzed by L-fuculose-1-phosphate aldolase, followed by reaction with acid phosphatase and L-fucose isomerase. The L-fucose product was isolated by Dowex® 50W-X8 ($Ba^{2+}$ form) chromatography, optionally combined with separation by silica gel (Wong et al., 1995; J. Org. Chem., 60:7360-7363).

EP 0 102 535 A2 discloses a process for the production of deoxysugars selected from fucose and rhamnose by fermentation using the genera *Alcaligenes, Klebsiella, Pseudomonas* or *Enterobacter*, which produce extracellular polysaccharides containing more than 10% fucose and/or rhamnose. It is disclosed that fucose and/or rhamnose may be recovered from the hydrolyzate of the fermentation product by chromatography, ion-exchange or adsorption (for example with zeolites) or by further fermentation treatment.

Similarly, a bacterial strain from the family Enterobacteriaceae has been found able to produce L-fucose containing polysaccharides under aerobic fermentation conditions, from which the fucose has been separated and isolated by acidic hydrolysis and many purification steps (WO 2012/034996 A1).

Lower cost ways of producing fucosylated lactoses have, however, been sought, such as by fermentation with transformed *E. coli* (Drouillard et al., 2006, Angew. Chem, Int. Ed. 45, 1778; WO 2010/070104 A1; WO 2010/142305 A1; WO 2012/097950 A1, WO 2012/112777 A2; Baumgartner et al., 2013, Microb. Ceil Fact. 12:40).

WO 2015/032412 A1 discloses a method of making a mixture of 2'-fucosyllactose (2'-FL) and difucosyllactose (DFL) in high yield by culturing a genetically modified cell having a recombinant gene that encodes a single fucosyltransferase in presence of lactose. The resulting mixture of 2'-FL and DFL can be subjected to hydrolysis initiated by an acid or mediated by a fucosidase to produce L-fucose in high yields.

WO 2016/150629 A1 shows a method for the biocatalytic and/or fermentative production of L-fucose by using L-fucitol as raw material. To convert L-fucitol to L-fucose in a one-step reaction, galactose oxidase is used after isolation in a biocatalytic step or directly inside the producing cells in vivo.

WO 2016/120448 A1 describes a process for fermentative production of L-fucose. Disclosed is a process for producing a monosaccharide, e.g. L-fucose, in free form using a microbial fermentation process. The used microorganism exhibits a hydrolase activity on intracellular produced nucleotide-activated sugars and releases the monosaccharide in an unmodified free form. L-fucose in free form is transported to the culture supernatant.

The existing attempts to provide a purified L-fucose have only involved small-scale demonstrations, but no process for purification of L-fucose to food-grade purity and food-grade quality from a fermentation broth in large scale is available to date.

SUMMARY

It was an object of the present invention to provide a process for a large-scale (industrial-scale) purification of L-fucose at a high degree of purity. Specifically, the process should be suitable for providing L-fucose in kg-scale to ton-scale in food-grade quality and should be suitable for being run in a continuous manner.

The object is solved by the process according to claim 1, the composition according to claim 18, the food composition according to claim 21, the liquid, ready-to-use infant or toddler nutrition product according to claim 28, the spray-dried infant formula product according to claim 29, the dietary supplement according to claim 30, the premix according to claim 31 and the use of the composition according to claim 33. The dependent claims illustrate advantageous embodiments.

According to the invention, a process for the purification of L-fucose from a fermentation broth is provided. The process comprises the following steps:
removing biomass from a fermentation broth comprising L-fucose, wherein a clarified solution is provided,
providing a purified solution by subjecting the clarified solution to
  a cationic ion exchanger treatment with a cationic ion exchanger material, wherein the cationic ion exchanger treatment is performed under conditions in which the L-fucose passes the cationic ion exchanger material and is present in the flow-through; and
  an anionic ion exchanger treatment with an anionic ion exchange material, wherein the anionic ion exchanger treatment is performed under conditions in which the L-fucose passes the anionic ion exchanger material and is present in the flow-through; and removing salts from the purified solution by electrodialysis and/or nanofiltration.

BRIEF DESCRIPTION OF THE DRAWINGS

The patent or application file contains at least one drawing executed in color. Copies of this patent or patent application with color drawing(s) will be provided by the Office upon request and payment of the necessary fee.

DETAILED DESCRIPTION OF A PREFERRED EMBODIMENT

Figure 1:
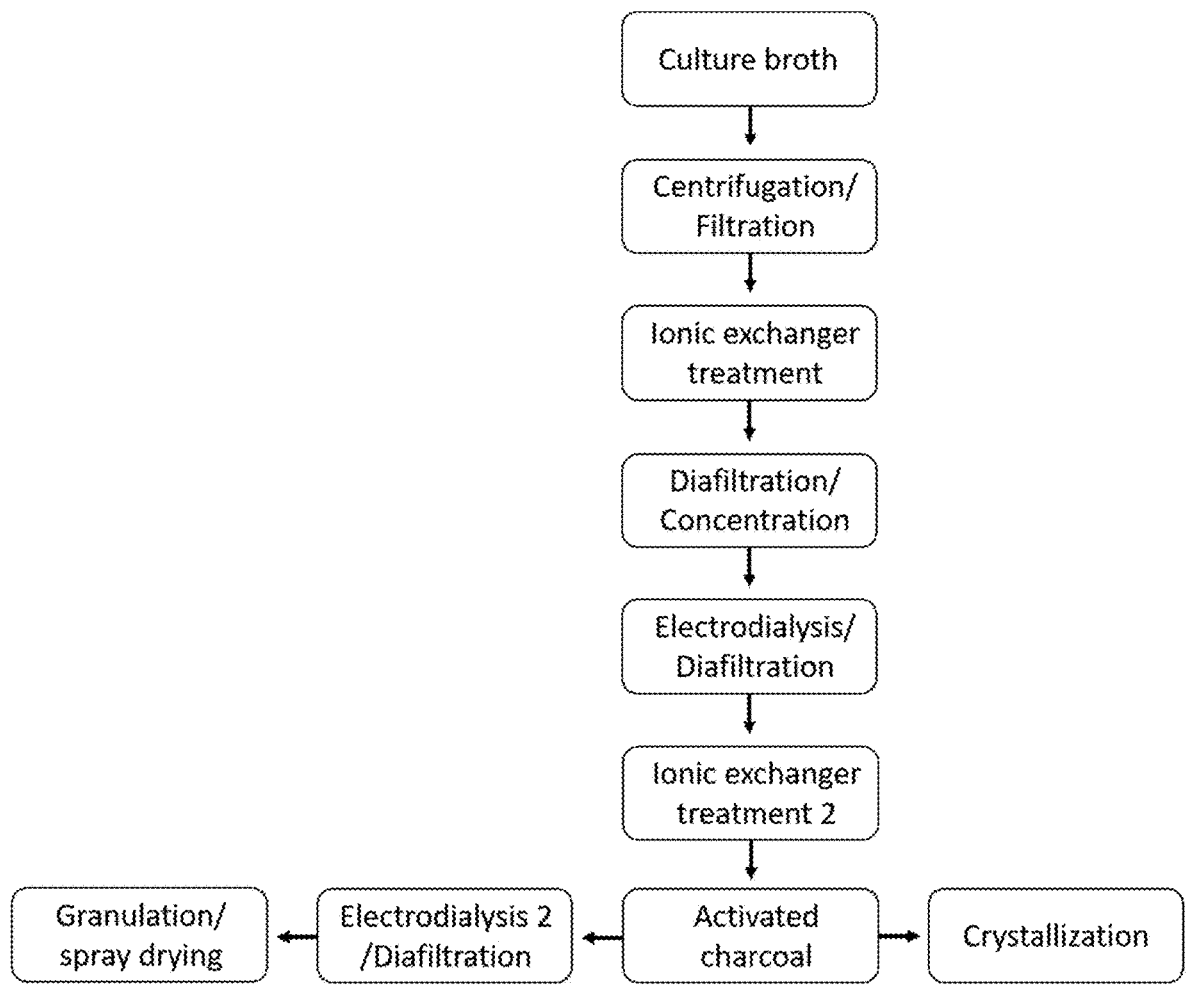
FIGS. 1-7 depict embodiments as described herein.

The inventive process is suitable for providing a desired L-fucose at a high degree of purity (food grade quality) and in large-scale (industrial-scale ranging from kg to tonnes per run). In addition, the inventive process can be carried out very fast and in an inexpensive manner. It can thus be run very economically. Furthermore, the process can be carried in a batch manner or in a continuous manner. The latter improves obtainable yield per time even further. At the end of the process, the purity of the L-fucose can be >80%, preferably >90%, more preferably >95%, most preferably at least 98%.

The presented process for purification of L-fucose is also advantageous in that the preparation of L-fucose is free of recombinant DNA and recombinant proteins derived from the recombinant microbial fermentation strains which are used for the production of L-fucose.

Notwithstanding that the inventive process was conceived for the purification of L-fucose from a fermentation broth, said process may also be used for the purification of L-fucose produced by an enzymatic reaction in vitro, a so-called in vitro biocatalysis reaction, or by using a permeabilized whole cell biocatalysis approach. It is understood that the purification of L-fucose from the reaction mixture of an in vitro biocatalysis reaction does not require removal of biomass from the reaction mixture. The reaction mixture of an in vitro biocatalysis reaction thus corresponds to the clarified process stream.

Definitions

According to the invention, the term "purity" refers to chemical purity and specifies the degree to which a substance, like L-fucose is undiluted or unmixed with extraneous material. Hence, the chemical purity is an indicator of the relationship between a single substance and by-products/impurities. Chemical purity is expressed as a percentage (%) and is calculated using the following formula:

$$\text{Percent Purity} = \frac{\text{Mass of desired compound in sample}}{\text{Total mass of sample}} \times 100\%$$

In a composition comprising L-fucose, the purity of L-fucose can be determined by any suitable method known to the skilled artisan, for example by using HPLC. An appropriate detector can be a detector selected from the group consisting of an electrochemical detector, a refractive-index (RI) detector, a mass-spectrometer (MS), a diode-array-detector (DAD) and an NMR detector. For example, in HPLC, the ratio of the area underneath the peak representing the amount of L-fucose to the sum of areas underneath the peaks representing both the amount of L-fucose and compounds different to L-fucose in the same chromatogram. However, this implies that all impurities can be analysed by the chosen HPLC method. Otherwise, a mass-balance approach, i.e. an absolute quantification of the desired product (e.g. L-fucose) is necessary. In said approach, pure substances are used as a reference for quantification of the purity, which is then judged against the dry-matter obtained from the product (desired product plus all impurities). Said mass-balance approach can also be used for determining purity according to the invention.

According to the invention, a "culture broth" refers to any liquid after fermentation which contains L-fucose to be purified. The terms "culture broth", "fermentation broth" and "culture medium" are used as synonyms herein. The culture broth comprises L-fucose which is to be purified as well as biomass (e.g. biological cells and cell debris), medium components, salts and contaminants like other acids and coloured compounds. The purity of the L-fucose within the culture broth can be <80%. The biological cells contained in the culture broth are biological cells which produce L-fucose intracellularly and secrete the produced L-fucose into the liquid culture medium. The biological cells can comprise or consist of genetically modified biological cells, for example genetically modified *E. coli* cells. The genetic modification can comprise or consist of a modification to produce L-fucose, especially during the growth phase of said biological cells.

The term "biomass" as used herein refers to the entirety of biological cells present in the fermentation broth at the end of the fermentation step. The biomass includes the cells of the microorganism that produced L-fucose, descendent cells of the microorganism that may have lost their ability to produce L-fucose during the fermentation step as well as any other cells that are unintentionally present in the fermentation broth at the end of the fermentation step. Hence, essentially all biological cells that are present in the fermentation broth at the end of the fermentation step are separated from the fermentation broth such that the clarified fermentation broth, i.e. the process stream, is substantially free of cells.

The term "process stream" refers to any solution comprising L-fucose which is to be purified.

The term "flow-through" refers to a solution comprising L-fucose which has just passed an ion exchanger material (i.e. a cationic and/or anionic exchanger material), i.e. is a mobile phase comprising L-fucose after a solid phase ion exchanger material has been contacted. In other words, L-fucose present in the flow-through has not adsorbed, or has not been absorbed, by the stationary phase.

According to this invention, the difference between a weak cationic ion exchanger material and a strong cationic ion exchanger material is that the chemical groups suitable for ion exchange of the former have a pKa of at least 1 (e.g. pKa from 2 to 5, like that of a carboxylate group) whereas the latter have a pKa of smaller than 1 (e.g. pKa from −4 to 0, like that of a sulfonic acid group).

Production of the Clarified Solution

The biomass preferably comprises biological cells which produce L-fucose, preferably bacterial cells which produce L-fucose, more preferably recombinant bacterial cells which produce L-fucose, most preferably recombinant *E. coli* cells, recombinant *Bacillus* sp. cells and/or recombinant *Corynebacterium* sp. cells, especially recombinant *Bacillus subtilis* and/or recombinant *Bacillus megaterium*, which produce L-fucose.

The biomass can be removed from the fermentation broth by centrifugation and/or filtration, wherein the filtration is preferably selected from the group consisting of microfiltration, ultrafiltration, cross-flow filtration, diafiltration and combinations thereof.

In suitable centrifugation methods for removing the biomass from the culture broth, the biomass is obtained as a pellet and the supernatant as clarified process stream which is subjected to further treatments. In suitable filtration methods for removing the biomass from the culture broth, the filtrate becomes the clarified process stream. The preferred filtration method for removing biomass is microfiltration and/or ultrafiltration. In ultrafiltration, even smaller particles than with microfiltration can be removed. Optionally, ultrafiltration is cross-flow ultrafiltration.

Microfiltration is a physical separation process wherein a particle-containing fluid is passed through a medium, said medium comprising either a porous substance containing torturous channels to retain particles (depth filtration) and/or a membrane with a specific pore size allowing the passage of particles/molecules that are smaller than said pore size (membrane filtration or dead-end filtration). The term "microfiltration" as used herein refers to a physical separation process wherein biological cells (and cell debris) are removed from the fermentation broth leaving a (clarified) process stream.

Ultrafiltration is a form of membrane filtration that is not fundamentally different from dead-end microfiltration. In ultrafiltration, forces generated by pressure and concentration gradients lead to the removal of particles and large soluble molecules by passing the liquid containing such particles and large soluble molecules through a semipermeable membrane causing the particles and large soluble molecules to be retained in the so-called retentate, while water and low molecular weight solutes such as L-fucose pass through the membrane into the permeate (filtrate). Membranes for ultrafiltration are defined by their molecular weight cut-off (MWCO) which describes the maximum molecular weight of a soluble molecule that can pass through the membrane in to the permeate. Any particles, as well as molecules larger than the MWCO, are unable to pass through the membrane remain in the retentate. Ultrafiltration may be applied in cross-flow mode, where the flow of the liquid is parallel to the membrane surface, or in dead-end mode where the flow of the liquid is perpendicular to the membrane surface.

Non-limiting examples and suitable filters for microfiltration and/or ultrafiltration for removing the biomass from the fermentation broth include SPIRA-CEL® DS MP005 4333, which is a module comprising a polyethersulfone membrane which is spirally wound to provide a compact design and better performance and has a nominal pore size of 0.05 μm for ultrafiltration applications. Suitable membranes for removing the biomass by microfiltration may have a pore size of at least 0.2 μm. Alternatively, the removal of biomass could be done by microfiltration with membranes having a MWCO between 100 and 1000 KDa, preferably between 150 kDa and 500 kDa, to remove the biomass and additional cell debris like bigger proteins. For example FS10-FC FUS1582 (Microdyn-Nadir GmbH, Wiesbaden, DE), a hollow fibre ultrafiltration module using a polyethersulfone membrane (5 m$^2$) with a MWCO of 150,000 Dalton (150 kDa), can be used as alternative.

In an additional and/or alternative embodiment, smaller particles and large soluble molecules are removed from the clarified process stream by a cross-flow ultrafiltration. Here, the clarified process stream can be subjected to an ultrafiltration step using a filter having a MWCO of 10 kDa, for example Spira-Cel® DSUP010 (Microdyn-Nadir GmbH, Wiesbaden, DE), a spiral wounded ultrafiltration module using a polyethersulfone membrane (5.7 m$^2$) with a MWCO of 10,000 Dalton (10 kDa).

In summary, the following possibilities for the removal of the biomass from the fermentation broth can be employed in the present invention:

i) Harvest by centrifugation. Insoluble parts are removed from the culture broth in one step. Advantage: Fast removal of insoluble parts;

ii) Harvest by microfiltration. Insoluble parts and large molecules above a certain size are removed from the culture broth in one step. Spiral wound membranes or a hollow fibre cross-flow filter can be used in microfiltration. Microfiltration membranes can be used which have a molecular weight cut-off in the range of ≥500 kDa, more preferably in the range of ≥150 KDa. Advantage: Fast removal of insoluble parts and large molecules above a certain size;

iii) Harvest by ultrafiltration. Insoluble parts, large molecules and small molecules above a certain size are removed from the culture broth in one step. Spiral wound membranes or a hollow fiber cross-flow filter can be used in ultrafiltration. Ultrafiltration membranes can be used which have a molecular weight cut-off in the range of ≤100 kDa, more preferably in the range of ≤10 KDa. Advantage: Fast removal of insoluble parts, large molecules and small above a certain size;

iv) Harvest by centrifugation combined with microfiltration: Insoluble parts and large molecules above a certain size are removed from the culture broth in two steps. Spiral wound membranes or a hollow fibre cross-flow filter can be used in microfiltration. Microfiltration membranes can be used which have a molecular weight cut-off in the range of ≥500 kDa, more preferably in the range of ≥150 KDa. Advantage: Fast removal of insoluble parts and large molecules above a certain size without clogging of membranes or filters used in microfiltration;

v) Harvest by centrifugation combined with ultrafiltration: Insoluble parts, large molecules and small molecules above a certain size are removed from the culture broth in two steps. Spiral wound membranes or a hollow fibre cross-flow filter can be used in ultrafiltration. Ultrafiltration membranes can be used which have a molecular weight cut-off in the range of ≤100 kDa, more preferably in the range of ≤10 KDa. Advantage: Fast removal of insoluble parts, large molecules and small molecules above a certain size without clogging of membranes or filters used in ultrafiltration;

vi) Harvest by microfiltration combined with ultrafiltration step: Insoluble parts, large molecules and small molecules above a certain size are removed from the culture broth in two steps. Spiral wound membranes or a hollow fibre cross-flow filter can be used in microfiltration and/or ultrafiltration. Microfiltration membranes can be used which have a molecular weight cut-off in the range of ≥500 kDa, more preferably in the range of ≥150 KDa. Ultrafiltration membranes can be used which have a molecular weight cut-off in the range of ≤100 kDa, more preferably in the range of ≤10 KDa. Advantage: Fastest removal of insoluble parts, large molecules and small molecules above a certain size with reduced risk of clogging of membranes or filters used in ultrafiltration.

The clarified process stream comprising L-fucose usually may contain a substantial amount of undesired impurities including (but not limited to) monovalent ions, divalent ions, amino acids, polypeptides, proteins, organic acids, nucleic acids, monosaccharides and/or oligosaccharides.

Steps that are Preferably Absent in the Inventive Process

The inventive process may comprise one or more chromatographic separation steps. However, in preferred embodiments, the process can be characterized in that it does not require or comprises a chromatographic separation (e.g. no chromatographic fractionation is necessary). The advantage of not performing a chromatographic separation is that the process can be run faster and less expensive because the time and expense for preparing an elution solution, using it to elute L-fucose from a solid phase and pool fractions of the elution is dispensed with.

Furthermore, the inventive process can be characterized in that it does not comprise a use of methanol, n-propanol, isopropanol, 2-butanone and/or ethyl acetate, optionally does not require the use of an organic solvent. The advantage of not using an organic solvent is that it can be ensured that the final product, the final L-fucose or composition comprising L-fucose, is free of methanol, ethanol, n-propanol, isopropanol, 2-butanone and/or ethyl acetate, optionally free of any organic solvent. In addition, the process becomes less expensive, environmentally friendly and safer for workers.

Moreover, the inventive process can be characterized in that it does not comprise a step of eluting the L-fucose from a stationary phase with a solution comprising an organic solvent. The advantage is that it is possible to keep the purified L-fucose free of any organic solvent. In addition, the process becomes less expensive, environmentally friendly and safer for workers.

Besides, the inventive process can be characterized in that it does not require a use of a heavy metal. The advantage is that it can be ensured that the purified L-fucose is free of heavy metals.

The inventive process may comprise one or more steps of heating the process stream, preferably to a temperature of more than 45° C. However, in a preferred embodiment, the inventive process does not comprise a step of heating the fermentation broth, the clarified solution and/or the purified solution to a temperature of more than 45° C. The advantage is that compared to prior art processes which employ such a heat treatment step, energy for heating the respective solutions is saved which makes the process more economical and more ecological.

Cationic Ion Exchanger Treatment

Among other impurities, cations can be removed from the clarified process stream by the cationic ion exchanger treatment step of the inventive process, i.e. by applying at least one cation-exchange treatment to the clarified process stream. Specifically, the cations are exchanged to other cations which are bound to the material of the cationic ion exchanger (stationary phase) before the clarified process stream is applied to the cationic ion exchanger treatment step. Importantly, it has been found that the cationic ion exchanger treatment removes ammonia and a part of contaminating proteins from the clarified process stream.

In the cationic ion exchanger treatment step, the positively charged materials can be removed from the cell free culture broth as they bind to the resin. The aqueous solution of L-fucose is contacted in any suitable manner which allows the positively charged materials to be adsorbed onto the cation exchange material whereas the L-fucose passes through. The resulting liquid, after contacting with the cation exchange resin, contains water, defined cations (those that were immobilized on the cationic ion exchanger material before this step), anions, colouring substances and L-fucose.

The cationic exchanger treatment can be performed with a weak cationic ion exchanger material or with a strong cationic ion exchanger material, preferably it is performed with a strong cationic ion exchanger material.

In the cationic ion exchanger treatment of the inventive process, a strong cationic ion exchanger can be used. Suitable cation-exchange resins for removing positively charged compounds are strongly acidic cation-exchange resins such as resins that comprise a carboxylate group (weak cation exchanger) or sulfonic acid group (strong cation exchanger) attached to a solid backbone (e.g. a polystyrene backbone). Suitable resins include (but are not limited to) Lewatit® S2568(W) (Lanxess AG, Cologne, DE), Dowex® 50WX2 (Merck KGaA, Darmstadt, DE); Amberlite® IR-116 (Japan Organo Co., Ltd.) and Diaion™ SK-102 (Mitsubishi Chemical Industries, Ltd).

The cationic ion exchanger treatment step can be the first step after removal of biomass from the culture medium, i.e. the first step the clarified culture medium is subjected to.

Unspecific cations are preferably replaced by the specific cation $H^+$ or $Na^+$ If the unspecific cations are replaced by $H^+$, the pH of the flow-through is preferably adjusted to a pH of 6 to 8 before performing a further treatment step (e.g. the anionic ion exchanger treatment), most preferably by addition of NaOH to the flow-through.

In a preferred embodiment, the cationic ion exchanger material is present in the $H^+$ form, i.e. the ion exchanging ligand of the cationic ion exchanger material is protonated, before the clarified process stream is applied to the cationic ion exchanger. This effectuates that during cation exchange, cations within the clarified process stream are replaced by $H^+$. Therefore, the pH of the solution after said step (flow-through) is more acidic than the pH of the solution before said step. Preferably, prior to subsequent purification steps, the pH of the flow-through is elevated to a neutral or almost neutral pH value (e.g. ≥pH 6.5 and ≤pH 7.5). The elevation of the pH can be achieved by adding NaOH to the process stream.

The cation ion exchanger could be used with any alkali metal ($Li^+$, $Na^+$, $K^+$), alkaline earth metal (such as $Ca^{2+}$, $Mg^{2+}$), ammonium ion or carbonate ion as counter ion. Preferably, sodium ($Na^+$) is the counter ion of the cation ion exchanger. More preferably, hydrogen ($H^+$) is the counter ion. The advantage of hydrogen as counter ion is that upon contacting the cationic ion exchanger material, the protonated form of anions in the process stream is generated and these protonated anions are found in the flow-through, i.e. in the solution that has passed the cationic ion exchanger material. Subsequently, the protonated form of said anions can be neutralized by addition of a base (e.g. NaOH) to the product stream which converts the protonated form of said anions into a specific salt form (e.g. the sodium salt form). Having the anions in the sodium salt form is beneficial because sodium ions are relatively small cations and can be more easily removed by nanofiltration and/or electrodialysis than larger cations.

Preferably, the cationic exchanger treatment step is carried out before the anionic exchanger treatment step. However, in principle, the cationic ion exchanger treatment can also be carried out after the anionic exchanger treatment step.

The particle size of the cationic exchanger resin is preferably in the range between 0.1 and 1 mm. This particle size range allows an efficient flow of the used cell free culture broth while the charged materials are still effectively removed by the cation exchange resin. To ensure that an efficient exchange of ions can take place, the flow rate should be preferably between >0.5 and <2.5 fold of the bed volume, more preferably between >1.0 and <2.0 fold of the bed volume. The ion exchange treatment can be carried out in a conventional manner, e.g. batch-wise or continuously, preferably continuously.

The conditions under which L-fucose passes the cationic exchanger material can be established by adjusting the pH and/or salt concentration of the clarified solution, preferably by adjusting the pH of the clarified solution to a pH in the range of 6 to 8 and/or, if needed, adjusting the salt concentration.

After the cationic ion exchanger treatment and the anionic ion exchanger treatment, the purified solution can comprise L-fucose, colour-giving substances and salt, wherein the salt is preferably NaCl. According to a preferred embodiment of the invention, in the anionic ion exchanger treatment, an anionic exchanger material in the chloride form is used.

According to a further preferred embodiment of the invention, in the cationic ion exchanger treatment, a cationic ion exchanger material in the hydrogen form is used. It was discovered that using a cation exchanger in hydrogen form (W counter ion) is beneficial because a much better binding of salts and contaminating proteins is obtained compared to the cation exchanger material in any other form (counter ion #H$^+$). The use of hydrogen form provokes that the flow-through has a more acidic pH than the solution which was applied to the cationic ion exchanger treatment. However, said pH can easily be raised by the addition of a base, preferably NaOH, to a neutral pH, preferably a pH in the range of 6 to 8. A neutralization with NaOH is beneficial because the introduced sodium ions are relatively small and can be easily removed by nanofiltration and/or electrodialysis.

The particle size of the cationic exchanger resin should be selected to allow an efficient flow of the used cell free culture broth, while the charged materials are still effectively removed by the cation ion exchange resin. To ensure that an efficient exchange of ions can take place, the flow rate should be preferably between >0.2 and <2.0 fold of the bed volume, more preferably between >0.5 and <1.5 fold of the bed volume. The ion exchange treatment can be carried out in a conventional manner, e.g. batch-wise or continuously, preferably continuously.

The clarified solution can be subjected firstly to the cationic ion exchanger treatment and subsequently to the anionic ion exchanger treatment. This process sequence has the advantage that the cationic ion exchanger material can be in the W form to obtain strong binding of contaminating proteins and after neutralisation with a base (e.g. NaOH), the anionic ion exchanger material can be run with a solution comprising a defined salt form of anions in the process stream (e.g. anions in the Na$^+$ form).

Anionic Ion Exchanger Treatment

Preferably, the anionic exchanger treatment step is carried out after the cationic exchanger treatment step. However, in principle, it can also be carried out before the cationic exchanger treatment step, i.e. after the process stream was treated with the cationic ion exchanger.

The anionic exchanger step is performed to remove unspecific anions and replace them by specific anions, preferably by the specific anion Cl$^-$ or OH$^-$. If the unspecific anions are replaced by Cl$^-$, the pH of the flow-through is preferably adjusted to a pH of 6 to 8 before performing a further treatment step (e.g. removing salts from the purified solution by electrodialysis), most preferably by addition of NaOH to the flow-through.

Anions can be removed from the clarified process stream by an anionic ion exchanger treatment step of the inventive process, i.e. by applying at least one anion ion exchanger treatment to the clarified process stream. The anionic ion exchanger treatment step can be the first step after removal of biomass from the culture medium, i.e. the first step the clarified culture medium is subjected to. Preferably, the anionic ion exchanger treatment is performed in a step after a cationic ion exchanger treatment step.

The negatively charged materials can be removed from the process stream as they bind to the anionic ion exchanger resin. The aqueous solution comprising L-fucose is contacted in any suitable manner which allows the negatively charged materials to be adsorbed onto the anionic exchange material, whereas L-fucose passes through. The resulting liquid, after contacting with the anionic exchange resin, contains water, defined cations, defined anions, colouring substances and L-fucose. The conditions of the anionic ion exchanger step are such that L-fucose does not bind to the anion exchanger material, i.e. is present in the flow-through after having contacted the material.

At the beginning of the anionic ion exchanger treatment, the pH of the product stream is preferably adjusted to pH 6 to 8 (most preferably pH 7). The flow-through (product stream having passed the anionic ion exchanger material) can have a lower pH, e.g. a pH in the range of 4.5 and 6. At this pH, anions in the flow-through can be present in the protonated form. The pH of the flow-through can be elevated by adding a base, e.g. NaOH.

During anionic exchange, anions within the clarified process stream can be replaced by Cl$^-$. Therefore, the pH of the process stream becomes slightly more acidic. Preferably, the pH is increased prior to subsequent purification steps, preferably to achieve a neutral or almost neutral pH value (i.e. ≥pH 6.5 and ≤pH 7.5) of the process stream. More preferably, the increase in pH of the process stream is achieved by adding NaOH to the process stream.

The anionic exchanger can be a weak anionic ion exchanger or a strong anionic ion exchanger, preferably a strong anionic ion exchanger.

Suitable strongly basic anion exchange resins are resins that comprise a trimethyl ammonium group or a hydroxyethyl group attached to a solid backbone (e.g. a polystyrene backbone). Suitable resins include (but not limited to) Lewatit® S6368 A, Lewatit® 54268, Lewatit® 55528, Lewatit® S6368A (Lanxess AG, Cologne, DE), Dowex® AG 1x2, Dowex® 1x8, Purolite® Chromalite CGA100x4 (Purolite GmbH, Ratingen, DE), Amberlite® FPA51 (Dow Chemicals, MI, USA). Preferably, the anion exchange resin is present in chloride form. Suitable weak anion exchange resins are resins that comprise an amino group attached to a solid backbone (e.g. a polystyrene backbone).

The anionic ion exchanger could be used with any base as counter ion, e.g. HCO$_3^-$, I$^-$, Br$^-$, NO$_3^-$. Preferably, the counter ion is hydroxide (OH$^-$). More preferably, the counter ion is chloride (Cl$^-$). The advantage of using chloride as counter ion is that the Cl$^-$ anion is smaller than many other anions that are originally present in the fermentation broth. This effectuates that the chloride anion can be more easily removed from the process stream by electrodialysis and/or nanofiltration (e.g. diafiltration). The advantage of using the OH$^-$ anion as counter ion is that when the pH is neutralized with HCl in a step after the anionic ion exchanger treatment, the small anion chloride which can be more easily removed than other anions is introduced into the process stream.

The particle size of the anionic exchanger resin is preferably between 0.1 and 1 mm to allow an efficient flow of the used process stream, while the charged materials are still effectively removed by the anionic exchange resin. To ensure that an efficient exchange of ions can take place, the flow rate should be preferably between >0.5 and <2.5 fold of the bed volume, more preferably between >1.0 and <2.0 fold of the bed volume. The ion exchange treatment can be carried out in a conventional manner, e.g. batch-wise or continuously, preferably continuously.

The conditions under which L-fucose passes the anionic exchanger material can be established by adjusting the pH and/or salt concentration of the clarified solution, preferably by adjusting the pH of the clarified solution to a pH in the range of 6 to 8 and/or by adjusting the salt concentration, if needed. For example, it has been observed that if a solution comprising the L-fucose is subjected to the anionic ion exchanger treatment which originates from the flow-through of a cationic ion exchanger treatment with $H^+$ as counter ion and that has been adjusted to pH 6 to 8 by addition of NaOH, the salt concentration of the flow through is sufficiently high to avoid binding of L-fucose to the anionic ion exchange resin. However, it has been observed that contaminations (e.g. certain proteins, DNA and RNA molecules (in particular recombinant DNA and RNA molecules) and coloured substances) still bind to the anionic exchange resin under said conditions.

In a preferred embodiment, the purification process comprises a treatment with a cationic exchanger resin in hydrogen ($H^+$) form and an anionic exchanger resin in chloride ($Cl^-$) form. The cationic exchanger resin is preferably a strong cationic exchanger. The anionic exchanger can be a weak or strong anionic exchanger, preferably it is a strong anionic exchanger. Additionally, the anionic exchanger material can also be an absorber material. The treatment with both the cationic ion exchanger resin and the anionic ion exchanger resin allows removal of all unspecific ions from the product stream. The unspecific ions can thus be replaced by specific anions, preferably the sodium cation (e.g. introduced by neutralisation of the product stream with NaOH after a contact with a cationic ion exchanger material with $H^+$ as counter ion) and the chloride anion. The sodium cation and the chloride anion are both relatively small ions and can be removed by electrodialysis and/or nanofiltration (diafiltration) in a faster and more economical manner than larger ions.

Concentration of the Purified Solution

In a preferred embodiment, the solution after the ion exchanger treatment (flow-through) which comprises L-fucose is concentrated, preferably by nanofiltration, reverse osmosis and/or vacuum evaporation (e.g. by using a falling film evaporator, a rotating evaporator or a plate evaporator). Reverse osmosis and/or nanofiltration are the preferred methods (e.g. nanofiltration with a nanofiltration membrane having a size exclusion limit of ≥20 Å). Particularly preferred is nanofiltration and/or reverse osmosis. The advantage of nanofiltration over reverse osmosis is that nanofiltration achieves faster concentration and also achieves partly removal of salt ions. The advantage of nanofiltration and/or reverse osmosis over vacuum evaporation is that no caramelisation reactions occur with the L-fucose, i.e. no coloured caramel bodies are produced during concentration.

The purified solution is most preferably concentrated by nanofiltration, wherein most preferably a nanofiltration membrane is used which has a molecular weight cut-off in the range of 100 to 200 kDa. The advantage of this molecular weight cut-off is that L-fucose is held back whereas salt ions can pass through the membrane, i.e. a desalting is effected beside the concentration.

Prior to the concentration of the solution, L-fucose in the solution can have a concentration of ≤20% (w/w), ≤10% (w/w) or ≤5% (w/w).

In the process, the clarified solution and/or purified solution can be concentrated up to a concentration of ≥100 g/L, preferably ≥200 g/L, more preferably ≥300 g/L, of the L-fucose.

Furthermore, the clarified solution and/or purified solution can be concentrated by nanofiltration at a temperature of <80° C., preferably <50° C., more preferably 4° C. to 45° C., more preferably 10° C. to 40° C., even more preferably 15° C. to 30° C., most preferably 15° C. to 20° C.

Moreover, the clarified solution and/or purified solution can be concentrated by reverse osmosis at a temperature of 20° C. to 50° C., more preferably 30° C. to 45° C., most preferably 35° C. to 45° C.

Besides, the clarified solution and/or purified solution can be concentrated by nanofiltration at a pressure between >5 bar and <50 bar, preferably at a pressure between >10 bar and <40 bar, more preferably at a pressure between >15 and <30 bar.

Furthermore, the clarified solution and/or purified solution can be concentrated by reverse osmosis at a pressure between >5 bar and <100 bar, preferably at a pressure between >10 bar and <80 bar, more preferably at a pressure between >15 and <70 bar.

Reverse osmosis is a membrane filtration method which removes particles larger than 0.1 nm from the solution (process stream). Only water will be removed from the process stream whereas all other molecules like ions, sugar etc. will be concentrated inside the retentate. By using reverse osmosis, only a raise in the concentration of the L-fucose can be achieved, but no desalting thereof.

In an additional and/or alternative embodiment, the concentration step comprises at least one of the following parameters, optionally all of the following parameters:

i) concentration is performed up to a concentration of ≥100 g/L, preferably ≥200 g/L, more preferably ≥300 g/L of the L-fucose;
ii) concentration is performed at a temperature of <80° C., preferably 50° C., more preferably 4° C. to 45° C.; most preferably 4° C. to 40° C., if concentration is performed by nanofiltration;
iii) concentration is performed at a temperature of <50° C., preferably 20° C. to 45° C.; most preferably 30° C. to 45° C., more preferably 35° C. to 45° C., if concentration is performed by reverse osmosis and/or vacuum evaporation; and
iv) concentration is operated at a pressure between >5 bar and <50 bar, preferably at a pressure between >10 bar and <40 bar, more preferably at a pressure between >15 and <30 bar.

In a preferred embodiment of the invention, the solution comprising L-fucose is concentrated before the electrodialysis step using vacuum evaporation (e.g. by using a falling film evaporator or a plate evaporator), reverse osmosis or nanofiltration (e.g. nanofiltration with a nanofiltration membrane having a size exclusion limit of ≥20 Å), preferably using nanofiltration or reverse osmosis, more preferably using nanofiltration.

In a further preferred embodiment of the invention, the solution comprising L-fucose is concentrated after the electrodialysis step using vacuum evaporation (e.g. by using a falling film evaporator or a plate evaporator), reverse osmosis or nanofiltration (e.g. nanofiltration with a nanofiltration membrane having a size exclusion limit of ≥20 Å), preferably using nanofiltration or reverse osmosis, more preferably using nanofiltration.

Preferably, the solution comprising L-fucose is concentrated before an isolation of L-fucose in solid form (e.g. crystallized form or granulated form) is performed.

Removal of Salts

The process for purifying L-fucose comprises a step in which salts are removed from the solution, preferably removed from the clarified solution and/or purified solution. Removal of salts can be achieved by subjecting the solution to be desalted to nanofiltration and/or electrodialysis.

Nanofiltration is a membrane filtration method in which the membrane contains nanometer-sized pores. Nanofiltration membranes have pore sizes ranging from 1 to 10 nanometers. The pore size of nanofiltration membranes is smaller than the pore sizes of microfiltration and even smaller than the pore sizes of ultrafiltration membranes, but actually larger than the pore sizes of membranes used for reverse osmosis. Membranes for use in nanofiltration are predominantly created from thin polymer films. Materials that are commonly used include polyethylene terephthalate or metals such as aluminium. Pore densities may range from 1 to $10^6$ pores per $cm^2$. Nanofiltration is used in the method for the purification of L-fucose to increase the concentration of L-fucose in a solution, e.g. in the clarified solution and/or purified solution. Additionally, a desalting of the solution (process stream) occurs.

Suitable membranes for nanofiltration include polyamide or polypiperazine, thin-film composite membrane material providing a size exclusion in the range of 150 to 300 Da, for example Dow Filmtec™ NF270 (Dow Chemical Company, USA). Such membranes allow high flux. In particular, nanofiltration membranes with a molecular cut-off between 100 and 300 kDa are beneficial for raising the concentration of L-fucose in the process stream. Membranes having this molecular cut-off prevent passing of L-fucose through the membrane and have the advantage that they also effectuate a desalting because the salt (e.g. sodium chloride) which is present in the process stream after the treatment with the ion exchanger material(s) passes the membrane and is separated from L-fucose. Additional examples of suitable membranes for nanofiltration include Trisep® 4040-XN45-TSF (Microdyn-Nadir GmbH, Wiesbaden, DE), GE4040F30 and GH4040F50 (GE Water & Process Technologies, Ratingen, DE).

Nanofiltration was found to efficiently remove significant amounts of contaminants (e.g. salt ions) prior to an electrodialysis treatment of the solution containing L-fucose. Nanofiltration was also found to be efficient for the removal of low-molecular-weight contaminants from the clarified fermentation broth after removal of biomass from the fermentation broth (e.g. by an ultrafiltration step). The removal of low-molecular-weight components is beneficial for concentrating and demineralizing the solution comprising L-fucose prior to an ion exchange treatment. The use of nanofiltration for raising the concentration of the L-fucose results in lower energy and processing costs and better product quality due to reduced thermal exposure.

Electrodialysis combines dialysis and electrolysis and can be used for the separation and concentration of ions in solutions based on their selective electromigration through a semipermeable membrane. Industrial electrodialysis applications date back to the early 1960s when this method was used for the demineralization of cheese whey for inclusion in infant formula. Further applications of electrodialysis include the adjustment of the pH of beverages such as wines, grape must, apple juice and orange juice.

The desalination of brackish water for the production of drinking water and the demineralization of milk whey for infant food production are the most widespread applications of electrodialysis today. The basic principle of electrodialysis consists of an electrolytic cell comprising a pair of electrodes submerged into an electrolyte for the conduction of ions, connected to a direct current generator. The electrode connected to the positive pole of the direct current generator is the anode, and the electrode connected to the negative pole is the cathode. The electrolyte solution then supports the current flow, which results from the movement of negative and positive ions towards the anode and cathode, respectively. The membranes used for electrodialysis are essentially sheets of porous ion-exchange resins with negative or positive charge groups, and are therefore described as cationic or anionic membranes, respectively. The ion exchange membranes usually consist of a polystyrene matrix carrying a suitable functional group (such as sulfonic acid for cationic membranes or a quaternary ammonium group for anionic membranes) cross-linked with divinylbenzene.

The electrolyte can be, for example, an aqueous solution comprising sodium chloride, sodium acetate, sodium propionate and/or or sulfamic acid. The electrolyte surrounds the cathode and anode and serves to allow a flow of an electrical current within the cell. The electrodialysis stack is then assembled in such a way that the anionic and cationic membranes are parallel as in a filter press between two electrode blocks, such that the stream undergoing ion depletion is well separated from the stream undergoing ion enrichment (the two solutions are also referred to as the diluate (undergoing ion depletion) and concentrate (undergoing ion enrichment).

The heart of the electrodialysis process is the membrane stack, which consists of several anion-exchange membranes and cation-exchange membranes separated by spacers, installed between two electrodes. By applying a direct electric current, anions and cations will migrate across the membranes towards the electrodes generating a (desalted) diluate stream and a concentrate stream.

The pore size of the ion-exchange membranes for use in electrodialysis is small enough to prevent diffusion of the product from the diluate stream into the concentrate stream, driven by high concentration differences between the two streams. After separation from biomass and/or exchange of cations and/or anions, proteins and in particular recombinant DNA molecules (ranging in size from fragments to entire genomes) must be quantitatively removed from the desired product.

Electrodialyis is used to remove the ions from the aqueous solution whereas L-fucose will remain inside the process stream. An important advantage of electrodialysis is that recombinant DNA molecules can be completely removed from the solution comprising L-fucose. Additionally, it has been found that the amount of salt in the process stream could be reduced by electrodialysis significantly. In fact, it has been discovered that sodium chloride can be completely removed from the product stream. This has the advantage that a L-fucose can be provided that is devoid of salt like sodium chloride which prevents any negative influence that a presence of salt (e.g. sodium chloride) can have in the final product e.g. infant food.

Removal of salts (e.g. by electrodialysis) can be performed until a stable conductivity ($mS/cm^2$) between 0.2 and 10.0 $mS/cm^2$, preferably 0.4 and 5.0 $mS/cm^2$, more preferably 0.5 and 1.0 $mS/cm^2$ is reached. Furthermore, electrodialysis can be performed until the amount of salt (g/l)<10.0 g/l, preferably <5.0 g/l, more preferably <1.0 g/l, even more preferably ≤0.5 g/l, most preferably ≤0.4 g/l, especially ≤0.2 g/l is reached.

The electrodialysis can be run under neutral conditions or under acidic conditions. The difference between the two variants lies in the form of anions present in the process stream.

In neutral condition during electrodialysis, before starting the electrodialysis, the pH of the process stream can be adjusted with an acid, preferably with hydrochloric acid (HCl), or a base, preferably sodium hydroxide (NaOH), until a pH of 5.0 to 9.0, preferably 6.0 to 8.0, more preferably 6.5 to 7.5 is reached.

In an acidic condition during electrodialysis, before starting the electrodialysis, the process stream is acidified with an acid, preferably hydrochloric acid (HCl), until a pH of 1.0 to 3.0, preferably 1.5 to 2.5, more preferably 1.8 to 2.2 is reached. Electrodialysis is preferably performed until a stable conductivity ($mS/cm^2$) and pH is reached.

Electrodialysis can be performed until a stable conductivity ($mS/cm^2$) between 1.0 and 10.0 $mS/cm^2$, preferably 1.5 and 10.0 $mS/cm^2$, more preferably 2.0 and 8.0 $mS/cm^2$, is reached. During electrodialysis, the pH must be controlled and adjusted with a base, preferably with sodium hydroxide. Under neutral conditions, electrodialysis can be performed using bipolar membranes. In this case, L-fucose can be concentrated in a separate electrodialysis concentrate circuit. Thus, L-fucose can be enriched during electrodialysis.

In the process, after removing salts from the purified solution,
i) the amount of salt in the purified solution can be <10% (w/w), preferably <5% (w/w), more preferably <1% (w/w), even more preferably 0.5% (w/w), most preferably 0.4% (w/w), especially ≤0.2% (w/w); and/or
ii) the conductivity can be between 0.2 and 10.0 $mS/cm^2$, preferably between 0.4 and 5.0 $mS/cm^2$, more preferably between 0.5 and 1.0 $mS/cm^2$.

Discolouring of the Clarified and/or Purified Solution

The clarified solution and/or purified solution can be subjected to a step of discolouring, preferably by a treatment with activated charcoal and/or a treatment with a cationic ion exchanger and an anionic ion exchanger which are coupled in series.

The discolouring step can be performed
i) before or after a step of diafiltration and/or concentration of the clarified solution; and/or
ii) before or after a step of electrodialysis and/or diafiltration of the clarified solution.

Preferably, the discolouring step is performed after the electrodialysis step, especially in the case said step is performed by treatment with a cationic ion exchanger and an anionic ion exchanger (which are coupled in series). The advantage is that the cationic ion exchanger and an anionic ion exchanger can be run with a process stream that comprises a very low concentration of salt which effectuates that many electrically charged contaminations (e.g. electrically charged peptides and/or DNA molecules) bind to the ionic exchanger material while L-fucose remains unbound and is located in the flow-through. Thus, the purity of L-fucose regarding coloured substances and uncoloured, electrically charged substances can be significantly improved by this step. Optionally, said step is performed after a nanofiltration step and/or before the electrodialysis step.

The advantage of removing colour-giving substances by a treatment with activated charcoal compared to a treatment with a cationic ion exchanger and an anionic ion exchanger (which are coupled in series) is that both electrically charged and electrically uncharged (neutral) colour-giving substances can be removed and electrically uncharged (neutral) carbohydrates (e.g. oligosaccharides, monosaccharides) can be removed.

Activated carbon, also called activated charcoal, is a form of carbon that has been processed to have small, low-volume pores that increase the surface area available for adsorption. Typically, just one gram of activated carbon has a surface area greater than 3000 $m^2$ as determined by gas adsorption, due to its high degree of micro porosity.

A carbohydrate substance like a monosaccharide or oligosaccharide tends to be bound to the surface of charcoal particles from an aqueous solution. Interaction of oligosaccharides with activated charcoal is much stronger than interaction of monosaccharides. This behaviour is caused by their structure and effectuates that L-fucose is bound weaker, i.e. to a smaller amount, to the activated charcoal than a contaminating oligosaccharide. Besides oligosaccharides, coloured materials are adsorbed to the activated charcoal. Other water-soluble materials like salts are bound in a weaker manner and elute from the activated charcoal with L-fucose by washing the charcoal with water (after incubation). After the elution with water, the adsorbed oligosaccharides and coloured substances still remain bound to the activated charcoal. Therefore, removal of contaminating oligosaccharides and coloured contaminants is possible by the treatment step with activated charcoal. In summary, the activated charcoal step removes colorants, other impurities and reduces the amounts of water-soluble contaminants, such as salt.

Suitable activated charcoals for removing colour giving compounds, oligosaccharide or contaminates are (but not limited to) granulated activated charcoals like Norit® GAC830EN (Carbot Cooperation) and Epibon® Y 12×40 spezial (Donaucarbon) or powdered activated charcoal like Norit® DX1, Norit® SA2 (Carbot Cooperation) and Carbopal® MB 4 (Donaucarbon).

The removal of colour-giving substances by a treatment with a cationic ion exchanger and an anionic ion exchanger (which are coupled in series) has the advantage compared to a treatment with activated charcoal that not only colour-giving substances can be removed from the solution, but unspecific salt ions in the solution can be exchanged to specific salt ions like e.g. ($Na^+$ and $Cl^-$ electrically charged peptides can be removed. The advantage of said ion exchange is that the desalting process can become more efficient ($Na^+$ and $Cl^-$ small ions compared to other possible ions and thus may be removed more easily by a desalting treatment step). A further advantage is that a negative influence of certain unspecific salts on crystallisation of L-fucose can be avoided.

The ion exchanger treatment is performed such that the charged materials and the colour-giving substances are adsorbed onto the respective ionic exchange material whereas L-fucose passes the respective ionic exchange material, i.e. is located in the flow-through. The resulting liquid (flow-through) contains water, a small amount of defined ions, a reduced amount of colour-giving substances and L-fucose.

The cationic exchanger can be a weak cationic ion exchanger or a strong cationic ion exchanger, preferably it is a strong cationic ion exchanger.

Suitable cation-exchange resins are strongly acidic cation-exchange resins such as (but not limited to) Lewatit® S2568($H^+$) (Lanxess AG, Cologne, DE), Dowex® 50WX2

(Merck KGaA, Darmstadt, DE); Amberlite® IR-116 (Japan Organo Co., Ltd.) and Diaion™ SK-102 (Mitsubishi Chemical Industries, Ltd).

The cationic ion exchanger could be used with any alkali metal ($Li^+$, $Na^+$, $K^+$), alkaline earth metal (such as $Ca^{2+}$, $Mg^{2+}$), ammonium ion or carbonate ion as counter ion. Preferably, the sodium ion (Nat) is the counter ion.

The anionic exchanger can be a weak anion exchanger or a strong anionic exchanger, preferably it is a strong anionic ion exchanger.

Suitable anion exchange resins are strongly basic (type I) anion exchange resins such as (but not limited to) Lewatit® 56368 Å, Lewatit® 54268, Lewatit® 55528, Lewatit® 56368A (Lanxess AG, Cologne, DE), Dowex® AG 1x2, Dowex ° 1x8, Purolite® Chromalite CGA100x4 (Purolite GmbH, Ratingen, DE), Amberlite® FPA51 (Dow Chemicals, MI, USA). Preferably, the anion exchange resin is present in chloride form.

The anionic ion exchanger could be used with any base as counter ion, e.g. $HCO^-_3$, $I^-$, $Br$, $NO^-_3$. Preferably, hydroxide ($OH^-$) is used as counter ion. More preferably, chloride ($Cl^-$) is used as counter ion.

Within the coupled series of the cationic ion exchanger and the anionic ion exchanger, the anionic ion exchanger can be located upstream or downstream of the cationic ion exchanger. Preferably, the anionic ion exchanger is located downstream of the cationic ion exchanger in the coupled series. Thus, a solution passing the series firstly passes the cationic ion exchanger and then passes the anionic ion exchanger.

The pH of the process stream having passed the cationic ion exchanger and/or anionic ion exchanger (i.e. the respective flow-through) is preferably >2.0 and <10.0, more preferably >3.0 and 9.0, most preferably >4.0 and <8.0.

The particle size of the ionic exchanger resin should be selected to allow an efficient flow of the process stream, while the charged materials and the colour-giving substances are still effectively removed by the ion exchange resin. To ensure that an efficient exchange of ions can take place, the flow rate should be preferably between >0.2 and <2.0 fold of the bed volume, more preferably between >0.5 and <1.5 fold of the bed volume and most preferably >0.75 and <1.2 fold of the bed volume. The ion exchange treatment can be carried out in a conventional manner, e.g. batch-wise or continuously, preferably continuously.

However, in case an endotoxin-free strain (e.g. a *Bacillus* strain and/or a genetically engineered endotoxin-free strain) is used, a step of removing endotoxin might not be necessary.

Sterile Filtration and/or Removal of Endotoxins

In a preferred embodiment of the invention, the purified solution is sterile filtered and/or subjected to endotoxin removal, preferably by filtration of the purified solution through a ≤10 kDa filter module. As an example, the purified solution containing L-fucose is filter-sterilized and/or subjected to an endotoxin removal step by filtration of the purified solution through a 3 kDa filter or through a 6 kDa filter. The removal of endotoxins is necessary if L-fucose is intended for human consumption.

Providing a Granulated Form of L-Fucose

Food powder agglomeration is commonly used to improve the instant properties of granulated (e.g. spray-dried) products. This process is used when it is desirable to enlarge the product particles to improve their flowability and/or visual appearance.

In general, the main properties of granulates or agglomerates, such as size, porosity, solubility, wettability, shape and/or density, depend on the type of the agglomeration (granulation) process and on the operating conditions during agglomeration. Fluidized bed agglomeration is one of the processes suitable for producing agglomerates with high porosity and good mechanical resistance for handling and packaging.

The principles of operation of fluidized bed agglomeration consist of fluidization of particles by a hot air flow and surface particle wetting by liquid binder atomization. Collisions between wet particles on the fluid bed form liquid bridges and particle coalescence. On drying these particles, the bridges solidify resulting in a consolidation of the agglomerates.

According to the invention, the purified solution can be granulated, particularly granulated at a concentration of the L-fucose of 5-50% (w/w), preferably 10-40% (w/w), more preferably 15-35% (w/w).

The inlet temperature can be in the range of 50° C.-120° C., preferably 65° C.-110° C., more preferably 80° C.-100° C.

The outlet temperature (product temperature) can be in the range of 30° C.-80° C., preferably 35° C.-75° C., more preferably 40° C.-75° C.

The resulting granulate should have a dry loss preferably between 0.1 and 5% of material weight, more preferably between 0.5% and 2.5% of material weight, most preferably between 0.7% and 1.5% of material weight.

In a preferred embodiment, the granulated L-fucose has preferably at least 50% (w/w) of the material with a particle size between 150 μm and 1400 μm more preferably at least more than 60% (w/w) with a particle size between 150 μm and 1400 μm, most preferably more than 70% (w/w) with a particle size between 150 and 1400 μm.

The particle size can be determined by sieving the material through sieves having different pore sizes. For example, to obtain L-fucose as a material having a particle size of between 150 μm and 1400 μm a sieve having a mesh aperture diameter of 1400 μm and a sieve with a mesh aperture diameter of 150 μm can be used subsequently (in either order) to select for the material having the desired particle size.

Providing a Roll-Dried Form of L-Fucose

L-fucose can be provided in a roller-dried form. In this regard, the purified solution can be roller-dried, i.e. subjected to a roller-drying procedure.

Providing a Crystallized Form of L-Fucose

L-fucose can be provided in a crystallized form. A method for crystallizing of L-fucose from aqueous solutions will be described herein.

It has been discovered that L-fucose can be selectively crystallized from a biocatalyis approach using enzymes or fermentation (culture) broth.

In a preferred embodiment, the aqueous solution of L-fucose to be used for crystallisation has a carbohydrate content of more than 50% (w/w), preferably more than 60% (w/w), preferably more than 70% (w/w), particularly more than 80% (w/w).

Alternatively, the L-fucose concentration in the aqueous solution to be used for the crystallization is 650-950 g/l, preferably 800-880 g/l.

The above concentration ranges and ratios can be achieved in a conventional manner by concentrating the aqueous process stream from the culture broth, preferably after removing, e.g. cells, colour giving substances, salts and/or charged molecules from the culture broth by using previously described methods.

Concentration of the L-fucose containing solution can be achieved removing water by nanofiltration and/or vacuum evaporation (e.g. by using a rotating evaporator or a plate evaporator), preferably nanofiltration in combination with vacuum evaporation.

To start crystallization, seeding crystals can be added to said concentrated L-fucose solution at a temperature, between 20° C. and 50° C., preferably at 25° C.

In the concentrated solution, L-fucose has preferably a carbohydrate concentration particularly of >75% (w/w).

The solution comprising L-fucose can be incubated under vacuum, preferably at a pressure of <200 mbar, more preferably at a pressure of <100 mbar, particularly at a pressure of <50 mbar.

Furthermore, solution comprising L-fucose can be incubated at a temperature between 15° C. to 60° C., preferably between 20° C. to 45° C., more preferably between 25° C. to 40° C., particularly between 30° C. and 35° C.

Moreover, the solution comprising L-fucose can be incubated until the carbohydrate concentration is >85%, preferably >90%, or until a viscous crystallization pulp occurs.

The solution comprising L-fucose (crystallization mixture) can then be placed in a suitable crystallization vessel and incubated at room temperature (25° C.) for 12 to 96 hours until a solid crystallization mass has formed.

The crystallization mass can be mechanical broken and an organic solvent, e.g. methanol, acetone, isopropanol and/or ethanol, preferably ethanol, can be added to the crystal solution. In order to solve the L-fucose crystals, 1 kg of crystallization material is mixed with 0.5 to 3 l ethanol, preferably 0.7 to 2.0 l ethanol, more preferably 1.0 to 1.5 l ethanol.

L-fucose crystals can be removed from the liquid phase by filtering (with or without vacuum) or by centrifugation. To remove the remaining mother liquor, the crystals will be washed with an organic solvent e.g. methanol acetone, isopropanol and/or ethanol, preferably ethanol. To remove the remaining mother liquor, 1 kg of crystallized L-fucose is preferably washed with 0.5 to 3 l, preferably 0.7 to 2.0 l, more preferably 1.0 to 1.5 l ethanol.

The resulting crystals can be dried for 4 to 48 h, preferably 8 to 36 h, more preferably 12 to 24 h, or until no change in weight can be observed. The drying temperature is selected to be between 10° C. and 80° C., preferably between 20° C. and 70° C., more preferably between 30° C. and 60° C., particularly between 40° C. and 50° C.

For crystallization of L-fucose from an aqueous solution, a second alternative method for crystallizing of L-fucose from aqueous solutions by using organic solvents will be described herein.

In a preferred embodiment, the aqueous solution of L-fucose to be used for crystallisation has a carbohydrate content of more than 40% (w/w), preferably more than 50% (w/w), preferably more than 60% (w/w), particularly more than 70% (w/w).

Alternatively, the L-fucose concentration in the aqueous solution to be used for the crystallization can be 650-850 g/l, preferably 700-780 g/l.

The above concentration ranges and ratios can be achieved in a conventional manner by concentrating the aqueous process stream from the culture broth, preferably after removing e.g. cells, colour giving substances, salts and/or charged molecules from the culture broth by using previously described methods.

Concentration of the L-fucose containing solution can be achieved by removing water by nanofiltration and/or vacuum evaporation (e.g. by using a rotating evaporator or a plate evaporator). Preferably, nanofiltration is used in combination with vacuum evaporation.

After concentration of the solution comprising L-fucose, the solution has a L-fucose carbohydrate concentration of particularly >70% (w/w). In order to remove the remaining water from the crystallization approach, a 0.5 fold volume of butanol can be added to the solution. The crystallization approach can then be incubated under vacuum until an equal amount of added liquid has been removed by vacuum distilling.

In order to start crystallization, seeding crystals can be added to said concentrated L-fucose solution, wherein the solution is preferably at a temperature between 20° C. and 50° C., preferably at 25° C.

The crystallization can preferably be carried out at a pressure of <200 mbar, more preferably <100 mbar, particularly <50 mbar.

Furthermore, the crystallisation can be carried out at a temperature of the crystallisation solution of between 15° C. to 60° C., preferably between 20° C. to 45° C., more preferably between 25° C. to 40° C., particularly between 30° C. and 35° C.

Moreover, the crystallisation solution can be incubated until the carbohydrate concentration is >85%, preferably >90%, or until a viscous crystallization pulp emerges.

The crystallization mixture can then be placed in a suitable crystallization vessel and incubated at room temperature (25° C.) for 12 to 96 hours until a solid crystallization mass has formed.

The crystallization mass can be mechanically broken and an organic solvent, e.g. methanol, acetone, isopropanol and/or ethanol, preferably ethanol, can be added to the crystallization mass. In order to solve the L-fucose crystals, 1 kg of crystallization material is preferably mixed with 0.5 to 3 l ethanol, preferably 0.7 to 2.0 l ethanol, more preferably 1.0 to 1.5 l ethanol.

L-fucose crystals can be removed from the liquid phase by filtering with or without vacuum or centrifugation. For removing the remaining mother liquor, the crystals can be washed with an organic solvent, e.g. methanol acetone, isopropanol and/or ethanol, preferably ethanol. In order to remove the remaining mother liquor, 1 kg of crystallized L-fucose is preferably washed with 0.5 to 3 l, preferably 0.7 to 2.0 l, more preferably 1.0 to 1.5 l ethanol.

The resulting crystals can be dried for 4 to 48h, preferably 8 to 36 h, more preferably 12 to 24 h, or until no change in weight can be observed. The drying temperature can be selected between 10° C. and 80° C., preferably between 20° C. and 70° C., more preferably between 30° C. and 60° C., particularly between 40° C. and 50° C.

Providing a Lyophilized Form of L-Fucose

The purified solution comprising L-fucose can also be lyophilized. In said lyophilisation, the purified solution comprising L-fucose is frozen and then the pressure is reduced such that the frozen water sublimes directly from the solid phase to the gas phase. This method usually produces a hygroscopic L-fucose powder.

Compositions and Products Provided by the Invention

According to the invention, a composition is provided which comprises 1. at least 95 wt.-% of L-fucose;

2. at most 1 wt.-% organic solvent; and 3. at most 1 wt.-% salts.

In a preferred embodiment, the composition comprises
a) 95.50 to 100.00 wt.-% of L-fucose, preferably 98.00 to 100.00 wt.-% of L-fucose, more preferably 98.50 to 100.00 wt.-% of L-fucose, optionally 98.70 to 99.90 wt.-% of L-fucose; and/or
b) 0.00 to 1.00 wt.-% organic solvent, preferably 0.00 to 0.50 wt.-% organic solvent, more preferably 0.00 to 0.40 wt.-% organic solvent, optionally 0.10 to 0.20 wt.-% organic solvent; and/or
c) 0.00 to 1.00 wt.-% salts, preferably 0.00 to 0.50 wt.-% salts, more preferably 0.00 to 0.40 wt.-% salts, optionally 0.10 to 0.20 wt.-% salts.

Preferably, the composition comprises (only)
a) 0.00 to 0.50 wt.-% proteins, more preferably 0.00 to 0.40 wt.-% proteins, optionally 0.10 to 0.20 wt.-% proteins; and/or
b) 0.00 to 0.50 wt.-% DNA, more preferably 0.00 to 0.40 wt.-% DNA, optionally 0.10 to 0.20 wt.-% DNA.

The composition can be characterized in that the L-fucose is present in amorphous form or in crystalline form, preferably in granulate form or in crystalline form. The crystalline form is preferably the dihydrate crystal form.

Human milk is the best source of nutrition for an infant. Human milk contains free L-fucose. It is known that fucose can be taken up by humans and activated by means of the Fucose-Salvage-Pathway to GDP-fucose. GDP-fucose is then used for the synthesis of fucosylated glycans which are important in cell-cell commination processes such as immune-recognition and brain development.

A food composition, preferably an infant food formula, a toddler food formula or a medical nutrition product, is provided, wherein the food composition comprises L-fucose and a probiotic carbohydrate (e.g. galactooligosaccharide (GOS), fructoligosaccharide (FOS), inuline, maltodextrin, isomaltose, lactulose, etc.), or another monosaccharide (e.g. a sialic acid such as N-acetylneuraminic acid).

The food composition, preferably an infant food formula, a toddler food formula or a medical nutrition product, can comprise L-fucose and at least one human milk oligosaccharide.

The food composition can comprise at least one sugar selected from the group consisting of 2'-fucosyllactose, 3-fucosyllactose, lacto-N-tetraose, lacto-N-triose II, lacto-N-fucocopentaose I, lacto-N-fucopentaose III, lacto-N-fucopentaose V, difucosyllactose, lacto-N-neotetraose, 3'-sialyllactose, 6'-sialyllactose and sialylated lacto-N-neotetraose and lacto-N-tetraose derivatives.

The food composition can be
i) a liquid food composition and comprise L-fucose at a concentration of 1 mg/l to 2 g/l, more preferably at a concentration of 5 mg/l to 1.5 g/l, even more preferably at a concentration of 20 mg/l to 1 g/l, most preferably at a concentration of 50 mg/l to 0.7 g/l; or
ii) a solid food composition and comprise the L-fucose at a concentration of 5 mg/kg to 15 g/kg, more preferably at a concentration of 25 mg/kg to 10 g/kg, even more preferably at a concentration of 100 mg/kg to 10 g/kg, most preferably at a concentration of 375 mg/kg to 5.25 g/kg.

The food composition can comprise sialic acid (e.g. N-acetylneuraminic acid) at the same concentration (range) as the L-fucose (see above).

The food composition can comprise
i) at least one neutral human milk oligosaccharide, preferably at least one neutral human milk oligosaccharide selected from the group consisting of 2'-fucosyllactose, 3-fucosyllactose, lacto-N-tetraose and lacto-N-neotetraose, most preferably all of said neutral human milk oligosaccharides; and
ii) at least one acidic human milk oligosaccharide, preferably at least one acidic human milk oligosaccharide selected from the group consisting of 3'-sialyllactose and 6'-sialyllactose, most preferably all of said acidic human milk oligosaccharides; and
iii) a sialic acid (e.g. N-acetylneuraminic acid).

The composition can further comprise at least one substance, optionally all substances, selected from the group consisting of lactose, whey protein, biotin, skimmed milk, vegetable oil, skimmed milk powder, oil of *Mortierella alpine*, fish oil, calcium carbonate, potassium chloride, vitamin C, sodium chloride, vitamin E, iron acetate, zinc sulfate, niacin, calcium-D-panthothenate, copper sulfate, vitamin A, vitamin B1, vitamin B6, magnesium sulphate, potassium iodate, folic acid, vitamin K, sodium selenite and vitamin D.

The food composition can comprise at least one substance selected from the group consisting of a protein source, a vitamin, an oil, a mineral, an enzyme, a further carbohydrate and a probiotic strain.

The food composition can be a composition selected from the group consisting of a medical food composition, a dietary supplement, a sachet product, a liquid ready-to-use infant nutrition product, a liquid ready-to-use toddler nutrition product, a granulated product, a spray-dried infant formula product and combinations thereof.

Further provided is a liquid, ready-to-use infant or toddler nutrition product comprising L-fucose at a concentration of 1 mg/l to 2 g/l, a sialic acid (e.g. N-acetylneuraminic acid) (preferably at a concentration of 1 mg/l to 2 g/l) and
i) at least one neutral human milk oligosaccharide selected form the group consisting of 2'-fucosyllactose, 3-fucosyllactose, difucosyllactose, lacto-N-tetraose and lacto-N-neotetraose; and/or
ii) at least one acidic human milk oligosaccharide selected from the group consisting of 3'-sialyllactose or 6'-sialyllactose.

The invention also provides a spray-dried infant formula product comprising L-fucose at a concentration of 5 mg/kg to 15 g/kg, a sialic acid (e.g. N-acetylneuraminic acid) (preferably at a concentration of 5 mg/kg to 15 g/kg) and
i) at least one neutral human milk oligosaccharides selected form the group consisting of 2'-fucosyllactose, 3-fucosyllactose, difucosyllactose, lacto-N-tetraose and lacto-N-neotetraose; and/or
ii) at least one acidic human milk oligosaccharide selected from the group consisting of 3'-sialyllactose and 6'-sialyllactose.

Moreover, a dietary supplement is provided, comprising L-fucose and at least one neutral HMO selected from the group consisting of 2'-fucosyllactose, 3-fucosyllactose, difucosyllactose, lacto-N-triose II, lacto-N-tetraose and lacto-N-neotetraose, lacto-N-fucopentaose I.

According to the invention, a premix for a food product (e.g. premix for an infant or toddler food formula) is provided which comprises L-fucose and at least one substance selected from the group consisting of a protein source, a vitamin, an oil, a mineral, an enzyme, a further carbohydrate (e.g. a carbohydrate different to L-fucose already present in the premix) and a probiotic strain. More preferably, the premix comprises all of said substances.

The protein source can be selected from the group consisting of whey, corn soya blend (CSB), protein hydrolysates and combinations thereof.

The vitamin can be selected from the group consisting of vitamin A, thiamine, riboflavin, vitamin B12, folate and combinations thereof.

The oil can be selected from the group consisting of palm oil, DHA, arachidonic acid and combinations thereof.

The mineral can be selected from the group consisting of potassium chloride, potassium iodate, zinc oxide and combinations thereof.

The enzyme can be selected from the group consisting of amylase, amyloglcosidase and combinations thereof.

The carbohydrate can be selected from the group consisting of is selected from the group consisting of a human milk oligosaccharide (HMO), a galactooligosaccharide (GOS), inulin, a fructooligosaccharide (FOS), lactose, isomaltose, sialic acid, and combinations thereof.

The probiotic strain can be selected from the group consisting of *Lactobacillus, Bifidobacterium, Bacillus*, yeast and combinations thereof.

The premix can be in the form of a spray-dried, granulated or liquid (syrup) product.

According to the invention, a pharmaceutical composition, preferably a pharmaceutical composition for use in preventing or treating at least one of a viral infection, a bacterial infection (improved immune function), a memory loss, brain development and dysbiosis, is provided. The pharmaceutical composition comprises a composition according to the invention and optionally comprises at least one sugar different to L-fucose and/or at least one probiotic bacterial strain, wherein the at least one sugar is preferably at least one sugar selected from the group consisting of lactose, lactulose, inulin and sucrose.

All compositions according to the present invention (e.g. the food composition, the liquid, ready-to-use infant or toddler nutrition product, the spray-dried infant formula product, the dietary supplement and the premix) can be characterized by at least one of the following features:

The composition preferably comprises lactose.

In the case of a solid composition, the concentration of lactose can be 50 to 800 g/kg, preferably 100 to 750 g/kg, more preferably 200 to 700 g/kg, even more preferably 300 to 650 g/kg, most preferably 400 to 600, especially 440 to 560 g/kg.

In the case of a liquid composition, the concentration of lactose can be 10 to 95 g/L, preferably 20 to 90 g/L, more preferably 30 to 85 g/L, even more preferably 40 to 80 g/L, most preferably 50 to 75 g/L, especially 60 to 74 g/L.

It was found that having lactose in the composition is connected to a positive effect on the well-being of the person who consumes the composition as food. This effect is due to a combinatorial effect of lactose with the other ingredients which are present in the inventive composition (e.g. fucose, sialic acid, neutral HMO and acidic HMO). It is speculated that lactose together with the other ingredients act together to protect the body against pathogenic bacteria and to modulate inflammatory reactions within the gastrointestinal tract of the persons who consume the composition.

The composition preferably comprises a maximum amount of HMOs (acidic and neutral HMOs).

In the case of a solid composition, the maximum concentration of HMO can be in the range of 20 to 70 g/kg, preferably 25 to 65 g/kg, more preferably 30 to 60 g/kg, even more preferably 35 to 55 g/kg, most preferably 40 to 50, especially 42.2 to 48.1 g/kg.

In the case of a liquid composition, the maximum concentration of HMO can be 2.0 to 9.0 g/L, preferably 3.0 to 8.0 g/L, more preferably 4.0 to 7.0 g/L, even more preferably 4.5 to 6.5 g/L, most preferably 5.0 to 7.0 g/L, especially 5.7 to 6.5 g/L.

The composition preferably comprises a certain concentration of an HMO.

In the case of a solid composition, the concentration of 2'-FL can be 5 to 40 g/kg, preferably 10 to 35 g/kg, more preferably 12.5 to 30 g/kg, most preferably 15 to 25 g/kg, especially 18.5 to 22.2 g/kg.

In the case of a liquid composition, the concentration of 2'-FL can be 0.5 to 5.5 g/L, preferably 1.0 to 4.5 g/L, more preferably 1.5 to 4.0 g/L, most preferably 2.0 to 3.5 g/L, especially 2.5 to 3.0 g/L.

In the case of a solid composition, the concentration of 3'-FL can be 3.5 to 7.5 g/kg, preferably 4.0 to 7.0 g/kg, more preferably 4.5 to 6.5 g/kg, most preferably 5.0 to 6.0 g/kg, especially 5.5 to 5.9 g/kg.

In the case of a liquid composition, the concentration of 3'-FL can be 500 to 1000 mg/L, preferably 600 to 950 mg/L, more preferably 650 to 900 mg/L, most preferably 700 to 850 mg/L, especially 750 to 800 mg/L.

In the case of a solid composition, the concentration of LNT can be 7 to 15 g/kg, preferably 8 to 14 g/kg, more preferably 9 to 13 g/kg, most preferably 10 to 12 g/kg, especially 11.1 g/kg.

In the case of a liquid composition, the concentration of LNT can be 0.2 to 3.5 g/L, preferably 0.4 to 3.0 g/L, more preferably 0.8 to 2.5 g/L, most preferably 1.0 to 2.0 g/L, especially 1.5 g/L.

In the case of a solid composition, the concentration of 3'-SL can be 0.4 to 3.5 g/kg, preferably 0.8 to 3.0 g/kg, more preferably 1.0 to 2.5 g/kg, most preferably 1.4 to 2.0 g/kg, especially 1.48 to 1.7 g/kg.

In the case of a liquid composition, the concentration of 3'-SL can be 50 to 400 mg/L, preferably 100 to 350 mg/L, more preferably 150 to 300 mg/L, most preferably 180 to 250 mg/L, especially 200 to 230 mg/L.

In the case of a solid composition, the concentration of 6'-SL can be 0.5 to 3.5 g/kg, preferably 1.0 to 3.0 g/kg, more preferably 1.5 to 2.5 g/kg, most preferably 2.0 to 2.3 g/kg, especially 2.07 to 2.22 g/kg.

In the case of a liquid composition, the concentration of 6'-SL can be 100 to 500 mg/L, preferably 150 to 450 mg/L, more preferably 200 to 400 mg/L, most preferably 250 to 350 mg/L, especially 280 to 300 mg/L.

In the case of a solid composition, the concentration of LNnT can be 0.2 to 3.5 g/kg, preferably 0.4 to 1.8 g/kg, more preferably 0.8 to 1.4 g/kg, most preferably 1.0 to 1.2 g/kg, especially 1.11 g/kg.

In the case of a liquid composition, the concentration of LNnT can be 10 to 350 mg/L, preferably 20 to 300 mg/L, more preferably 50 to 250 mg/L, most preferably 100 to 200 mg/L, especially 150 mg/L.

In the case of a solid composition, the concentration of LNFP-I can be 1.0 to 10.0 g/kg, preferably 3.0 to 9.0 g/kg, more preferably 6.0 to 8.0 g/kg, most preferably 7.0 to 7.5 g/kg, especially 7.4 g/kg.

In the case of a liquid composition, the concentration of LNFP-I can be 0.1 to 2.0 g/L, preferably 0.3 to 1.5 g/L, more preferably 0.6 to 1.2 g/L, most preferably 0.8 to 1.1 g/L, especially 1.0 g/L.

In the case that the composition is a premix, the above-mentioned concentrations can be at least 2 times, preferably at least 4 times, more preferably at least 8 times, even more preferably at least 16 times, most preferably at least 20 times, especially at least 22 times higher.

Exemplary Food Composition

The inventive process provides the desired L-fucose of sufficient purity to allow its use in food or feed applications, in particular useful for inclusion into infant and toddler nutrition products. The obtained L-fucose can used for the preparation of an infant formula by mixing it with components of an infant base formula. The infant formula can be a powder formula or a ready-to-use liquid infant formula.

The base formula can have at least one, optionally all, of the following components:

Base Formula: Components of a Representative Base Formula:
Skimmed milk
Vegetable oils (palm oil, rapeseed oil, sunflower oil)
Skimmed milk powder
Oil of *Mortierella alpine*
Fish oil
Calcium carbonate
Potassium chloride
Vitamin C
Sodium chloride
Vitamin E
Iron acetate
Zinc sulfate
Niacin
Calcium-D-panthothenate
Copper sulfate
Vitamin A
Vitamin B1
Vitamin B6
Magnesium sulfate
Potassium iodate
Folic acid
Vitamin K
Sodium selenite
Vitamin D Use of the Inventive Composition A use of the inventive composition in the manufacture of a food composition and/or pharmaceutical composition is suggested.

With reference to the following figures and examples, the subject according to the invention is intended to be explained in more detail without wishing to restrict said subject to the special embodiments shown here.

FIG. 1 shows an example of an inventive process for purification of L-fucose. After fermentation, the fermentation broth is clarified by centrifugation and/or filtration. The clarified fermentation broth is subjected to an ionic exchanger treatment for removal of electrically charged contaminations and for exchange of unspecific ions to specific ions. The flow-through of the ionic exchanger treatment is then subjected to diafiltration and/or concentration. After said step, the solution comprising L-fucose is subjected to electrodialysis and/or diafiltration. Then, the solution comprising L-fucose is subjected to a further ionic exchanger treatment for removal of electrically charged colored substances and peptides. Subsequently, the solution comprising L-fucose is subjected to an activated charcoal treatment. Then, the solution is either subjected to crystallization of L-fucose or subjected to a further electrodialysis and/or diafiltration step with subsequent granulation and/or spray-drying.

Figure 2:
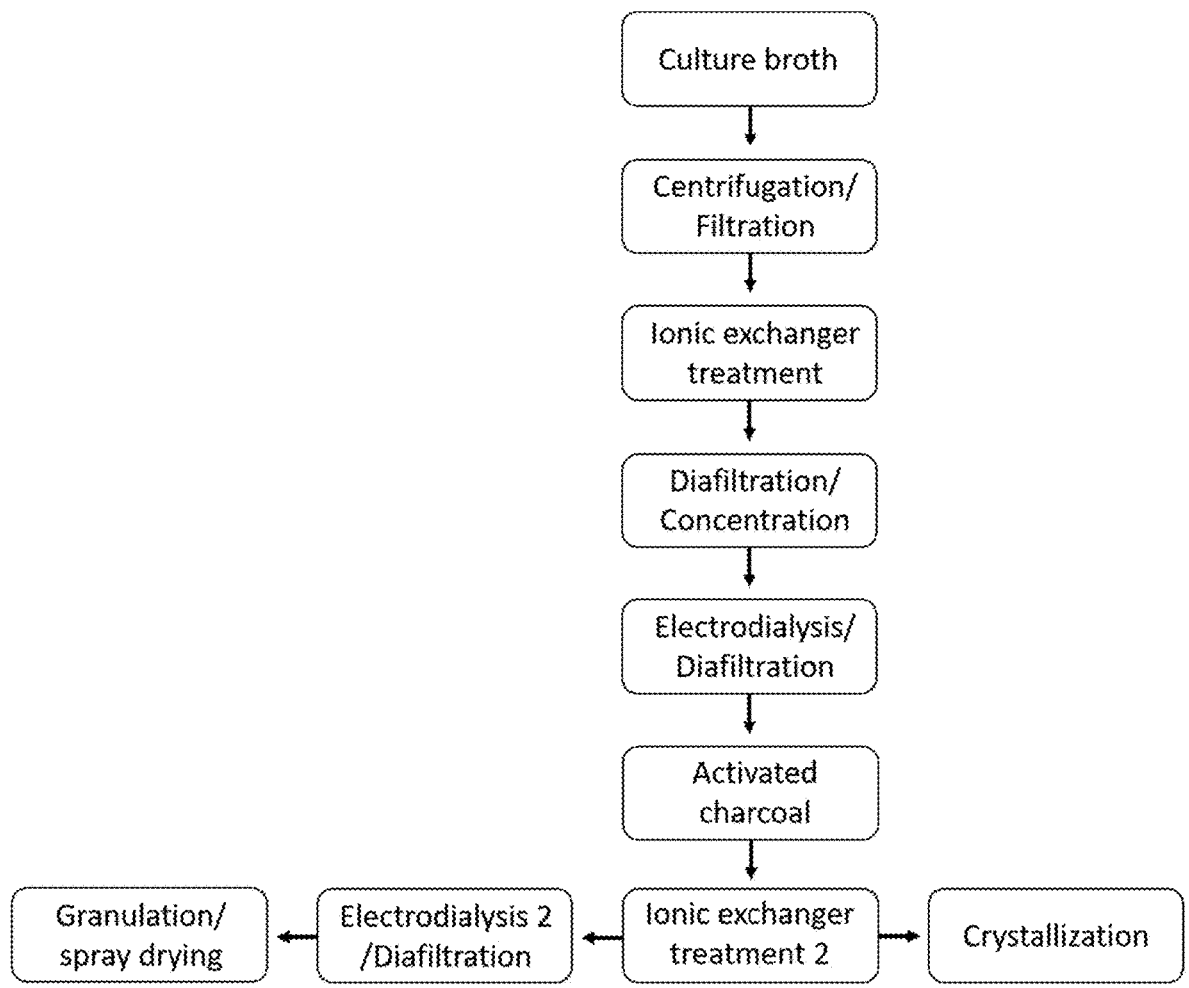

FIG. 2 shows an example of a second inventive process for purification of L-fucose. After fermentation, the fermentation broth is clarified by centrifugation and/or filtration. The clarified fermentation broth is subjected to an ionic exchanger treatment for removal of electrically charged contaminations and for exchange of unspecific ions to specific ions. The flow-through of the ionic exchanger treatment is then subjected to diafiltration and/or concentration. After said step, the solution comprising L-fucose is subjected to electrodialysis and/or diafiltration. Then, the solution comprising L-fucose is subjected to an activated charcoal treatment. Subsequently, the solution comprising L-fucose is subjected to a further ionic exchanger treatment for a removal of electrically charged colored substances and peptides. Then, the solution is either subjected to crystallization of L-fucose or subjected to a further electrodialysis and/or diafiltration step with subsequent granulation and/or spray-drying.

Figure 3:
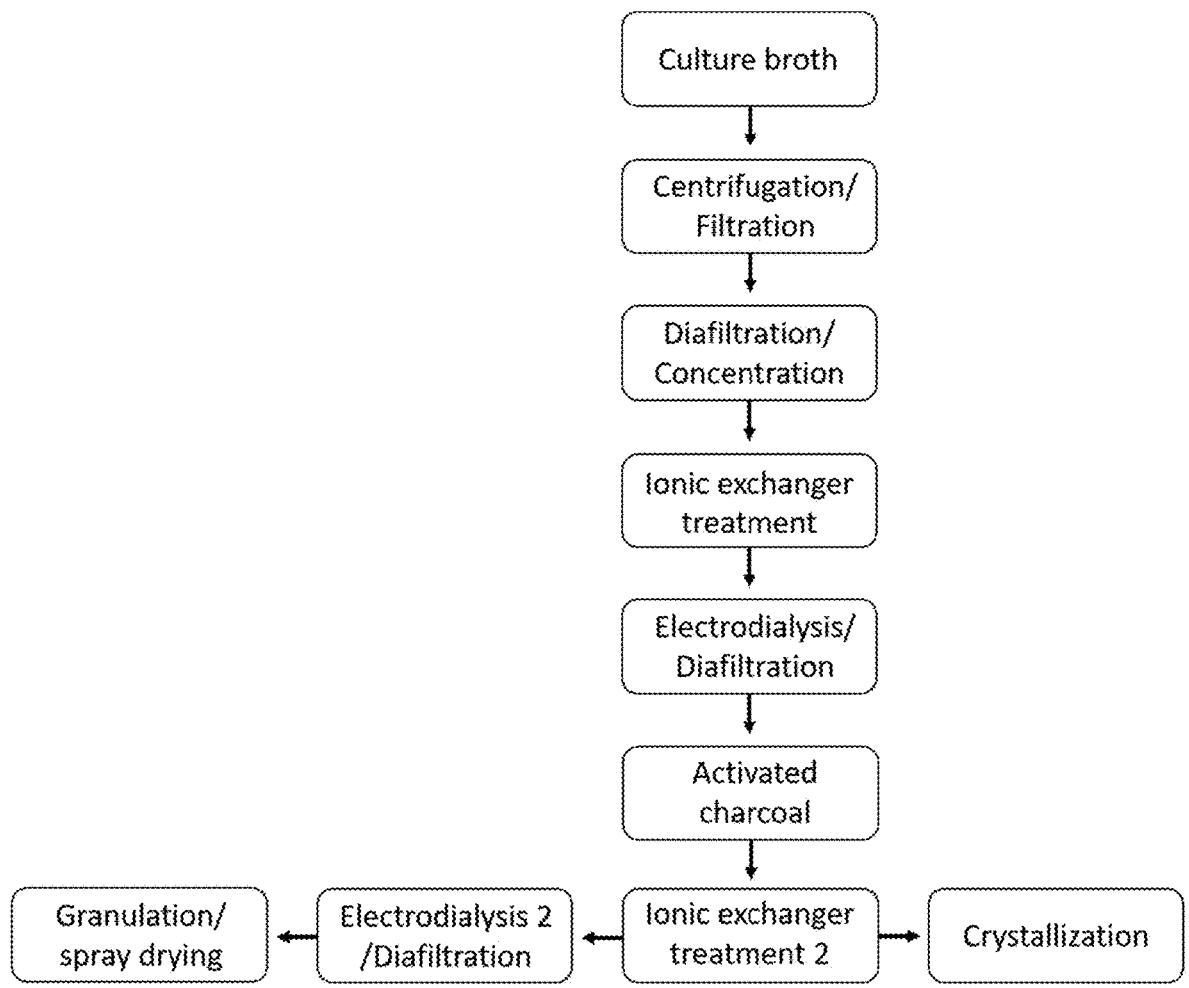

FIG. 3 shows an example of a third inventive process for purification of L-fucose. After fermentation, the fermentation broth is clarified by centrifugation and/or filtration. The clarified fermentation broth is subjected to diafiltration and/or concentration. Then, the solution is subjected to an ionic exchanger treatment for removal of electrically charged contaminations and for exchange of unspecific ions to specific ions. After said step, the solution comprising L-fucose is subjected to electrodialysis and/or diafiltration. Then, the solution comprising L-fucose is subjected to an activated charcoal treatment. Subsequently, the solution comprising L-fucose is subjected to a further ionic exchanger treatment for a removal of electrically charged colored substances and peptides. Then, the solution is either subjected to crystallization of L-fucose or subjected to a further electrodialysis and/or diafiltration step with subsequent granulation and/or spray-drying.

Figure 4:
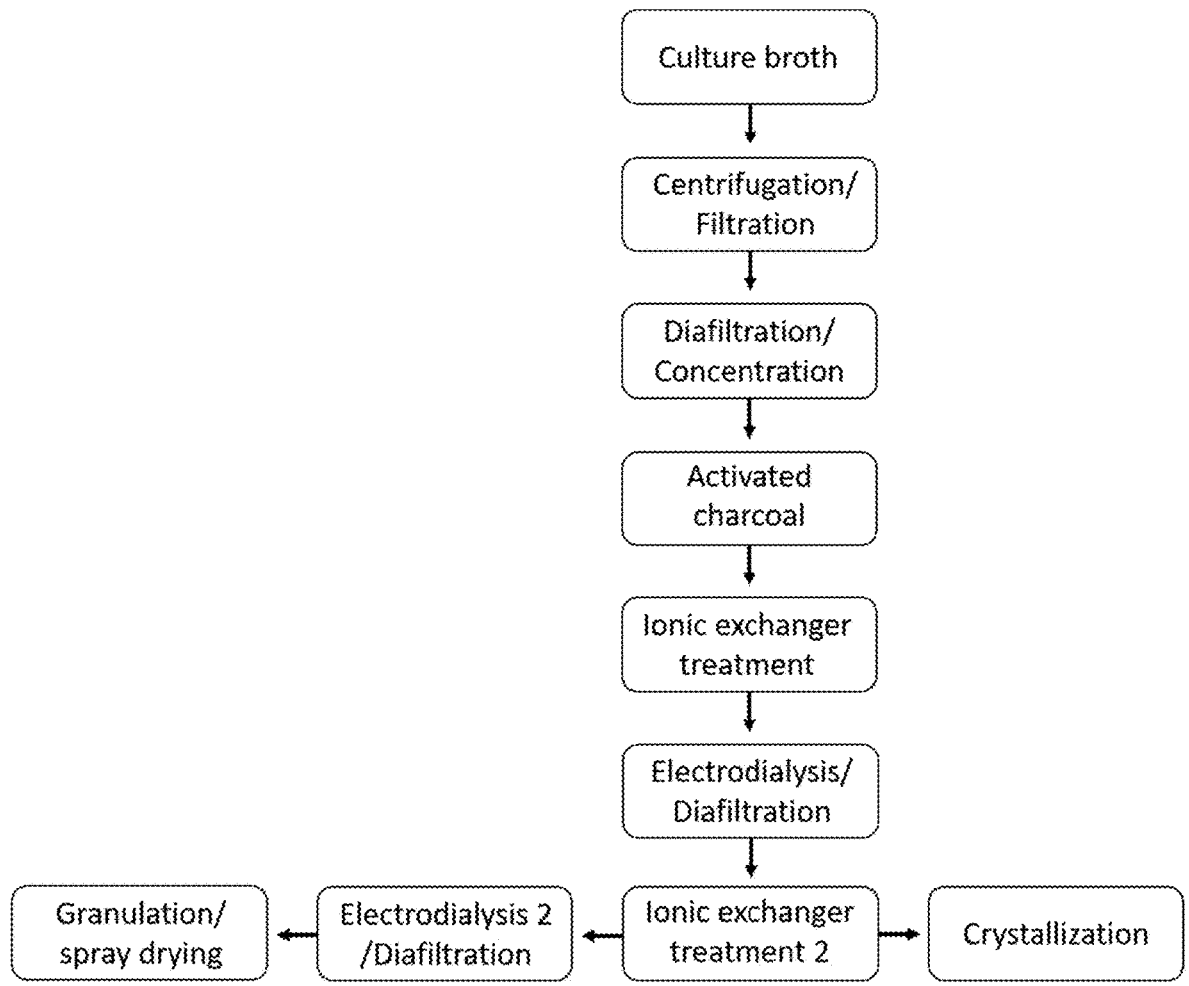

FIG. 4 shows an example of a fourth inventive process for purification of L-fucose. After fermentation, the fermentation broth is clarified by centrifugation and/or filtration. The clarified fermentation broth is subjected to diafiltration and/or concentration. Then, the solution is subjected to an activated charcoal treatment. After said step, the solution comprising L-fucose is subjected to an ionic exchanger treatment for removal of electrically charged contaminations and for exchange of unspecific ions to specific ions. Subsequently, the solution comprising L-fucose is subjected to electrodialysis and/or diafiltration. Afterwards, the solution is subjected to a further ion exchanger treatment for a removal of electrically charged colored substances and peptides. Then, the solution is either subjected to crystallization of L-fucose or subjected to a further electrodialysis and/or diafiltration step with subsequent granulation and/or spray-drying.

Figure 5:
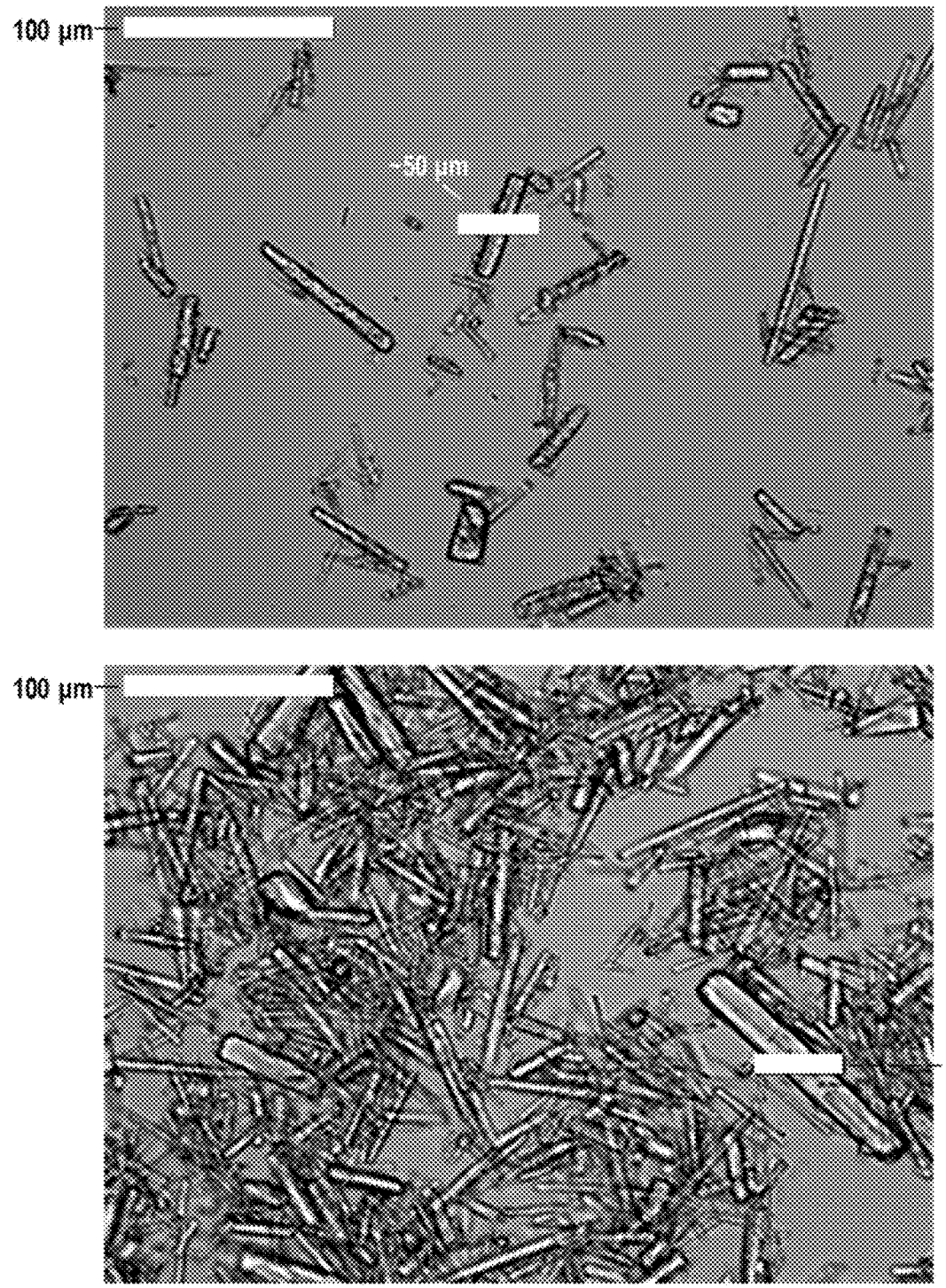

FIG. 5 shows a microscopic picture of crystals of L-fucose formed by crystallization from an aqueous solution. It can be seen that L-fucose forms needle-like crystals with a length of 50 μm to 150 μm.

Figure 6:
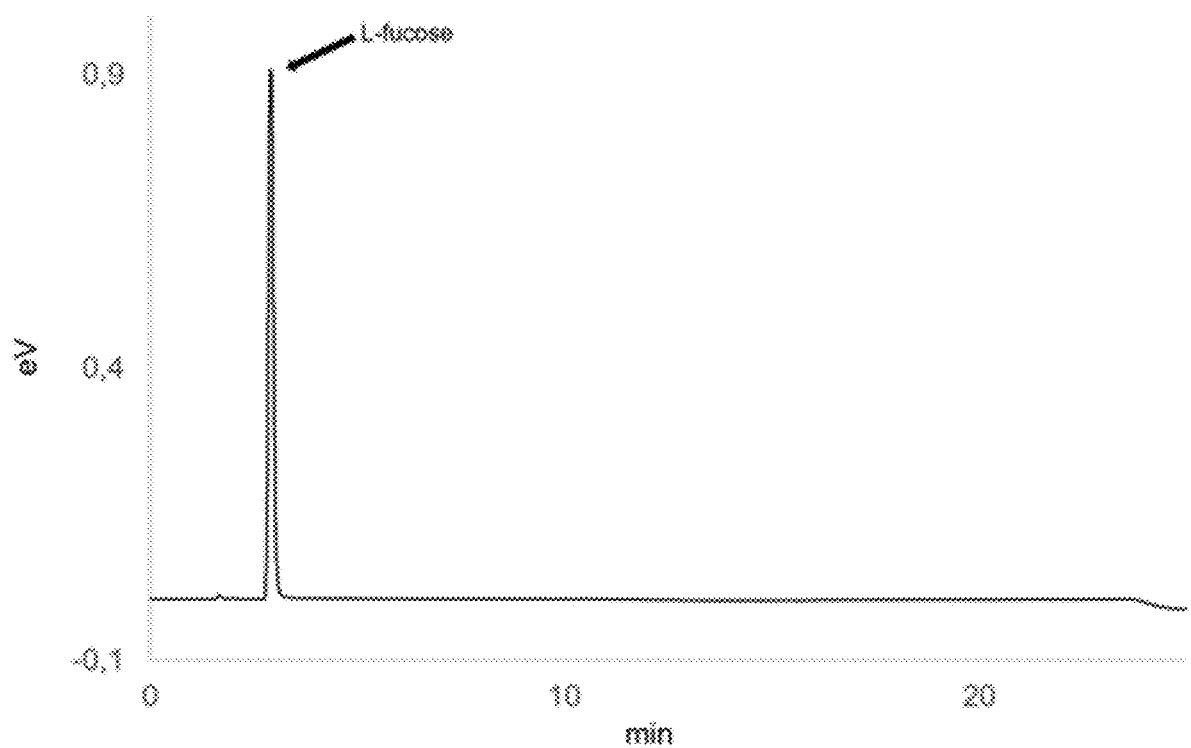

FIG. 6 shows an HPLC diagram which was recorded for L-fucose that has been crystallized from an aqueous solution. The purity of the crystallized L-fucose is detected as 99.8%. The water content is 0.1% (w/w).

Figure 7:
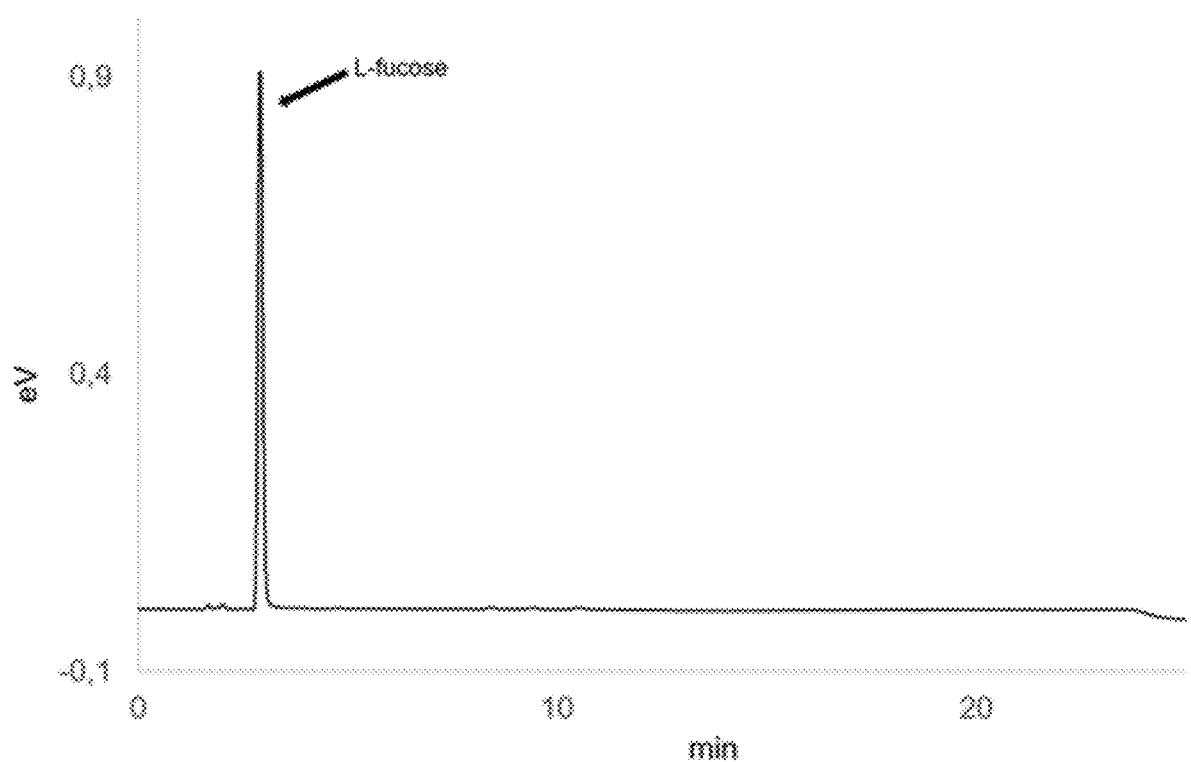

FIG. 7 shows an HPLC diagram which was recorded for L-fucose that has been granulated from an aqueous solution. The purity of the granulated L-fucose is detected as 97.8%. The water content is 1.7% (w/w).

EXAMPLE 1: PURIFICATION OF L-FUCOSE FROM BACTERIAL FERMENTATION

L-fucose was produced by a bacterial fermentation and harvested by filtration. The resulting clear particle-free L-fucose solution (34 g/l) was treated with a strong cationic ion exchanger (Lewatit® S2568 in proton form, Lanxess). After neutralization with sodium hydroxide, the solution was additionally processed with a strong anionic ion exchanger (Lewatit® S 6368A in chloride form).

For concentration of L-fucose after ionic exchanger treatment, the solution was further processed by a reverse osmosis step. An Emrich EMRO 1.8 reverse osmosis system (Emrich Edelstahlbau) was equipped with a Trisep® TS80 (80-40-TS80-TSA) nanofiltration module. The inlet pressure was set to 25 bar and the solution was concentrated until the L-fucose concentration has reached 100 g/l. Alternatively, the L-fucose solution could also concentrated by vacuum evaporation, nevertheless filtration techniques reduces the production of Maillard reactions during concentration.

To remove the sodium chloride from the ion exchanger step and other ions the solution was electrodialysed using a PCCell P15 electrodialysis system (PCell, Heusweiler, Germany) equipped with a PCCell ED 1000A membrane stack. Said stack comprised the following membranes: cation exchange membrane CEM: PC SK and the anion exchange membrane CEM:PcAcid60 having a size exclusion limit of 60 Da. The conductivity of the starting solutions was between 15 and 25 mS/cm$^2$ and the solution was electrodialysed until the conductivity was 1.5 to 2 mS/cm$^2$.

After electrodialysis, the solution was treated again with a strong cationic ion exchanger (Lewatit® 52568 in sodium form, Lanxess) and a strong anionic ion exchanger (Lewatit® S 6368A in chloride form) to remove a colored substances and possibly remaining unspecific ions (like e.g. peptides).

For a more rigorous removal of colored substances, the L-fucose containing solution was further treated with activated carbon powder. The solution was incubated for 2 hours under stirring with Norit DX1 activated charcoal. After incubation, the activated carbon was removed by filtration.

After activated carbon treatment, the L-fucose containing solution was concentrated by reverse osmosis filtration using an Emrich EMRO 1.8 reverse osmosis system (Emrich Edelstahlbau) which was equipped with a CSM RE8040BE reverse osmosis module. The solution was concentrated until the flow rate of the filtration system drops below 50 liter/hours. The dry matter after concentration was between 30 and 35% (w/w).

Alternatively, the L-fucose could be also concentrated by vacuum evaporation. This technique leads to a higher concentration (50 to 60% (w/w) of L-fucose. The disadvantage of concentration by vacuum evaporation is that L-fucose will partly undergo caramelization which is evidenced by the solution turning into a distinct brown color. In short, product quality, product purity and product yield are decreased by this concentration method.

EXAMPLE 2: CRYSTALLIZATION OF L-FUCOSE BY USING ORGANIC SOLVENTS

For crystallization of L-fucose, 15 liters of a 32% (w/w) solution were concentrated to a final concentration of 80 to 85% (w/w) dry matter by vacuum evaporation using an Hei-VAP industrial evaporator (Heidolph Instruments GmbH, Schwabach Germany) to obtain a mother liquor for crystallization of L-fucose.

To start the crystallization process, the mother liquor was inoculated with seed crystals. Additional 2.5 liters (ratio Butanol to fucose 1:2) of n-butanol were added and the solution was concentrated under vacuum until the solution was saturated with crystals.

The crystallization mass was removed from the piston and incubated for at least 24 hours until a solid crystallization mass was obtained.

The solid crystals were mixed with ethanol in a ratio of 1 to 1 (1 liter ethanol with 1 kg crystallization mass). To remove the mother liquor and the ethanol from the crystals, the solution was centrifuged.

The crystals were washed again with ethanol (2.5 liters for 5 kg L-fucose crystals) and centrifuged again. The solid L-fucose crystals were removed from the centrifuge and dried at 40° C. until no ethanol was left. The L-fucose was sifted through a riddle with 0.2 mm diameters.

At the end, 3.3 kg L-fucose was obtained from 5 kg L-fucose crystallization approach (yield: 66%).

EXAMPLE 3: CRYSTALLIZATION OF L-FUCOSE FROM AQUEOUS SOLUTIONS

For crystallization of L-fucose from aqueous solutions, 15 liters of a 32% (w/w) solution were concentrated to a final concentration of 80% to 85% (w/w) dry matter by vacuum evaporation using an Hei-VAP industrial evaporator (Heidolph Instruments GmbH, Schwabach Germany).

To start the crystallization process, the mother liquor was inoculated with seed crystals. The solution was concentrated under vacuum until a clear crystal formation was observed.

The crystallization mass was removed from the piston and incubated for at least 72 hours until a solid crystallization mass was obtained. The solid crystals were mixed with ethanol in a ratio of 1 to 1 (1 liter ethanol with 1 kg crystallization mass).

To remove the mother liquor and the ethanol from the crystals, the solution was centrifuged. The crystals were washed with ethanol (2.5 Liter for 5 kg L-fucose crystals) and centrifuged again. The solid L-fucose crystals were removed from the centrifuge and dried at 40° C. until no ethanol was left. The L-fucose was sifted through a riddle with 0.2 mm diameters.

At the end, 3.0 kg L-fucose was obtained from 5 kg L-fucose crystallization approach (yield: 60%).

EXAMPLE 4: ISOLATION OF L-FUCOSE BY GRANULATION

For granulation of L-fucose, a fluid bed system from Glatt (Glatt GmbH, Germany) was used. From a crystallization approach of L-fucose, a 40% (w/w) L-fucose solution was provided and used for granulation in the fluid bed system.

The fluid bed system was equipped with a total of 500 g of solid L-fucose and the system was started by adding the feed solution. The system was stabilized by a product temperature between 45° C. and 50° C. After 300 g L-fucose, the first agglomerates were formed. After addition of 1000 g 40% (w/w) L-fucose solution (400 g L-fucose), the system was stopped and analysed.

After granulation and a recovery rate of 80%, 720 g L-fucose could be recovered with a bulk density of 570 g/l and a dry loss of 0.9%. The size of the granulated L-fucose was analysed by sieving. This test shows that 70% of the material has a size between 150 μm and 1400 μm.

EXAMPLE 5: PURITY DEGREES IN AN EXEMPLARY PURIFICATION OF L-FUCOSE

The purity degrees in an exemplary purification of L-fucose from culture broth are shown in Table 1.

TABLE 1

Purification of L-fucose from culture broth. Purity is declared as the mass of L-fucose in comparison to the total mass.

| Purification step | Concentration L-fucose (g/l) | L-fucose (kg) | Dry Matter (kg) | Purity (%) |
|---|---|---|---|---|
| Harvest | 33 | 204 | 298 | 68 |
| Cationic exchanger | 31 | 199 | 281 | 70.8 |
| Anionic exchanger | 29 | 189 | 302 | 62.5 |
| Concentration | 88 | 186 | 269 | 69.1 |
| Electrodialysis | 86 | 156 | 161 | 96.9 |
| Activated carbon | 81 | 149 | 154 | 96.7 |
| Concentration | 310 | 150 | 154 | 97.4 |
| Crystallization |  | 86.3 |  | 98.8 |

EXAMPLE 6: COMPOSITION OF A REPRESENTATIVE INFANT FORMULA PRODUCT

In the following, a composition of a representative infant formula product is presented (see Table 2 below).

The composition comprises L-fucose in combination with the abundant neutral HMOs 2'-fucosyllactose (2'-FL), 3-fucosyllactose (3-FL), lacto-N-tetraose (LNT) and optionally lacto-N-neotetraose (LNnT) and lacto-N-fucopentaose I (LNFP-I), acidic HMOs (6'-sialyllactose (6'-SL) and 3'-sialyllactose (3'-SL)), and the sialic acid N-acetylneuraminic acid (Neu5Ac).

One or more probiotic strains can be present in the product. The final concentration of each ingredient is based on a preparation of 13.5 g of the powder in 90 ml of water.

TABLE 2

Comparison of a representative infant formula product

|  |  | per 100 g powder | per 100 ml infant formula |
|---|---|---|---|
| Energy | kJ | 2094-2145 | 283 |
|  | kcal | 500-512 | 67-68 |
| Fats, | g | 24.2-26.2 | 3.3-3.5 |
| hereof: |  |  |  |
| saturated fatty acids | g | 8.7-9.4 | 1.2-1.3 |
| monounsaturated fatty acids | g | 10.4 | 1.4 |
| polyunsaturated fatty acids | g | 5.5-5.9 | 0.7-0.8 |
| Carbohydrates | g | 56-58 | 7.4-7.9 |
| Sugars | g | 44-56 | 6-7.4 |
| hereof: |  |  |  |
| Lactose | g | 44-56 | 6-7.4 |
| Sialic acid (Neu5Ac) | mg | 300-450 | 40-60 |
| L-fucose | mg | 300-450 | 40-60 |
| HMOs | g | 4.22-4.81 | 0.57-0.65 |
| Hereof |  |  |  |
| 2'-FL | g | 1.85-2.22 | 0.25-0.30 |
| 3'-FL | mg | 555.56-592.6 | 75-80 |
| LNT | g | 1.11 | 0.15 |
| LNnT | mg | 0-111.11 | 0-15 |
| LNFP-I | mg | 0-740.74 | 0-100 |
| 3'-SL | mg | 148.15-170.37 | 20-23 |
| 6'-SL | mg | 207.4-222.22 | 28-30 |
| Protein | g | 11.11-11.85 | 1.5-1.6 |
| Salt | g | 0.47-0.59 | 0.06-0.08 |
| Vitamins |  |  |  |
| Vitamin A | µg | 357-358 | 47.3-48.2 |
| Vitamin D | µg | 7.8 | 1.05 |
| Vitamin E | mg | 8.15 | 1.1 |
| Vitamin K | µg | 43.7-44.4 | 5.9-6.0 |

TABLE 2-continued

Comparison of a representative infant formula product

|  |  | per 100 g powder | per 100 ml infant formula |
|---|---|---|---|
| Vitamin C | mg | 115-118 | 15-16 |
| Vitamin B1 | mg | 0.51-0.60 | 0.068-0.079 |
| Vitamin B2 | mg | 1.3-1.7 | 0.18-0.23 |
| Niacin | mg | 3.63 | 0.49 |
| Vitamin B6 | µg | 526-600 | 71-81 |
| Folic acid | µg | 160-164 | 21.6-21.7 |
| Vitamin B12 | µg | 1.7-1.9 | 0.23-0.25 |
| Biotin | µg | 22-30 | 3.0-3.9 |
| Panthothenic acid | mg | 4.6-5.4 | 0.62-0.72 |
| Minerals |  |  |  |
| Sodium | mg | 187-236 | 25.3-31.2 |
| Potassium | mg | 673-675 | 88.8-91.2 |
| Chloride | mg | 327-333 | 43.1-44.9 |
| Calcium | mg | 460-504 | 62.1-66.5 |
| Phosphorous | mg | 335-352 | 45.2-46.5 |
| Magnesium | mg | 49.3-56.3 | 6.66-7.43 |
| Iron | mg | 4.15 | 0.56 |
| Zinc | mg | 3.7-3.8 | 0.49-0.51 |
| Copper | µg | 274 | 37 |
| Manganese | µg | 96.3 | 13 |
| Fluoride | µg | 30.4-32.6 | 4.1-4.4 |
| Selenium | µg | 11.1-12.3 | 1.5-1.6 |
| Iodine | µg | 101.5-103.7 | 13.7-14 |

EXAMPLE 7: COMPOSITION OF A REPRESENTATIVE PREMIX FOR AN INFANT FORMULA PRODUCT COMPRISING HUMAN MILK OLIGOSACCHARIDES, THE MONOSACCHARIDE L-FUCOSE AND THE MONOSACCHARIDE N-ACETYLNEURAMINIC ACID (NEU5AC)

In the following, a composition of a representative premix for an infant formula product is presented (see Table 3 below).

The composition comprises the monosaccharide L-fucose in combination with the abundant neutral HMOs 2'-fucosyllactose (2'-FL), 3-fucosyllactose (3-FL), lacto-N-tetraose (LNT) and optionally lacto-N-neotetraose (LNnT) and lacto-N-fucopentaose I (LNFP-I) and acidic HMOs (such as 6'-sialyllactose (6'-SL), 3'-sialyllactose (3'-SL) and sialylated LNT derivatives), and the sialic acid N-acetylneuraminic acid (Neu5Ac).

The premix can be used to reconstitute an infant formula by adding said premix to other nutritional products which are necessary to reconstitute an infant food formula, such as whey, lactose, lipids (saturated and unsaturated fatty acids) and minerals. The premix shown in Table 3 is intended to be used for 1 kg of final infant formula product.

TABLE 3

HMO/Sialic acid/Fucose Vitamin premix

| Sialic acid (Neu5Ac) | g | 3.0 |
| L-fucose | g | 3.0 |
| 2'-FL | g | 18.5 |
| 3-FL | g | 5.5 |
| LNT | g | 10.0 |
| 3'-SL | g | 1.5 |
| 6'-SL | g | 2.0 |

TABLE 3-continued

HMO/Sialic acid/Fucose
Vitamin premix

| Vitamins | | |
|---|---|---|
| Vitamin A | mg | 3.5 |
| Vitamin D | µg | 78.0 |
| Vitamin E | mg | 81.5 |
| Vitamin K | µg | 437.0 |
| Vitamin C | g | 1.1 |
| Vitamin B1 | mg | 5.1 |
| Vitamin B2 | mg | 13.0 |
| Niacin | mg | 36.3 |
| Vitamin B6 | mg | 5.2 |
| Folic acid | mg | 1.6 |
| Vitamin B12 | µg | 17.0 |
| Biotin | µg | 220.0 |
| Panthothenic acid | mg | 46.0 |

The invention claimed is:

1. A process for the purification of L-fucose from a fermentation broth, comprising:
    removing biomass from a fermentation broth comprising L-fucose, wherein a clarified solution is provided,
    providing a purified solution by subjecting the clarified solution to
        a cationic ion exchanger treatment and
        an anionic ion exchanger treatment; and
    removing salt from the purified solution by electrodialysis and/or nanofiltration.

2. The process according to claim 1, wherein the cationic ion exchanger treatment is performed under conditions in which L-fucose passes the cationic ion exchanger material and is present in the flow-through and wherein the anionic ion exchanger treatment is performed under conditions in which L-fucose passes the anionic exchanger material and is present in the flow-through.

3. The process according to claim 1, wherein the biomass
    i) is removed from the fermentation broth by centrifugation and/or filtration; and/or
    ii) comprises cells which produce L-fucose.

4. The process according to claim 1, wherein the cationic ion exchanger treatment, a strong cationic ion exchanger is used and/or in the anionic ion exchanger treatment, a strong anionic exchanger is used.

5. The process according to claim 1, wherein the cationic ion exchanger treatment is performed to remove unspecific cations and replace them by specific cations.

6. The process according to claim 1, wherein the anionic exchanger step is performed to remove unspecific anions and replace them by specific anions.

7. The process according to claim 1, wherein conditions under which the L-fucose passes the anionic exchanger material and cationic exchanger material are established by adjusting the pH and/or salt concentration of the clarified solution.

8. The process according to claim 1, wherein the cationic ion exchanger treatment and the anionic ion exchanger treatment, the purified solution comprises the L-fucose, one or more color-giving substances and salt, wherein the salt is optionally NaCl.

9. The process according to claim 1, wherein the anionic ion exchanger treatment, an anionic exchanger material in the chloride form is used and/or in the cationic ion exchanger treatment, a cationic exchanger material in the hydrogen form is used.

10. The process according to claim 1, wherein the clarified solution is subjected firstly to the cationic ion exchanger treatment and subsequently to the anionic ion exchanger treatment.

11. The process according to claim 1, wherein the purified solution is concentrated.

12. The process according to claim 1, wherein the clarified solution and/or the purified solution is concentrated
    i) up to a concentration of ≥100 g/L, optionally ≥200 g/L, optionally ≥300 g/L, of L-fucose; and/or
    ii) by nanofiltration at a temperature of <80° C., optionally <50° C., optionally 4° C. to 45° C., optionally 10° C. to 40° C., optionally 15° C. to 30° C., optionally 15° C. to 20° C.; and/or
    iii) by reverse osmosis at a temperature of 20° C. to 50° C., optionally 30° C. to 45° C., optionally 35° C. to 45° C.; and/or
    iv) by nanofiltration at a pressure between >5 bar and <50 bar, optionally at a pressure between >10 bar and <40 bar, optionally at a pressure between >15 and <30 bar; and/or
    v) by reverse osmosis at a pressure between >5 bar and <100 bar, optionally at a pressure between >10 bar and <80 bar, optionally at a pressure between >15 and <70 bar.

13. The process according to claim 1, wherein the electrodialysis is an electrodialysis under neutral conditions or an electrodialysis under acidic conditions.

14. The process according to claim 1, wherein after removing salt from the purified solution,
    i) the amount of salt in the purified solution is <10% (w/w), optionally <5% (w/w), optionally ≤1% (w/w), optionally ≤0.5% (w/w), optionally ≤0.4% (w/w), especially ≤0.2% (w/w); and/or
    ii) the conductivity is between 0.2 mS/cm$^2$ and 10.0 mS/cm$^2$, optionally between 0.4 mS/cm$^2$ and 5.0 mS/cm$^2$, optionally between 0.5 mS/cm$^2$ and 1.0 mS/cm$^2$.

15. The process according to claim 1, wherein the clarified solution and/or purified solution is subjected to discolouring.

16. The process according to claim 1, wherein the purified solution is subjected to
    i) granulation;
    ii) spray-drying;
    iii) roller-drying; or
    iv) lyophilization.

17. The process according to claim 1, wherein the purified solution is subjected to crystallisation.

18. The process according to claim 3, wherein the filtration is selected from microfiltration, ultrafiltration, cross-flow filtration, diafiltration, and combinations thereof.

19. The process according to claim 3, wherein the cells which produce L-fucose are recombinant bacterial cells.

20. The process according to claim 19, wherein the recombinant bacterial cells are recombinant *E. coli* cells, recombinant *Bacillus* sp. cells and/or recombinant *Corynebacterium* sp. cells, especially recombinant *Bacillus subtilis* cells and/or recombinant *Bacillus megaterium* cells.

21. The process according to claim 5, wherein unspecific cations are replaced by the specific cation H$^+$ or Na$^+$.

22. The process according to claim 21, wherein if the unspecific cations are replaced by H$^+$, the pH of the flow-through is adjusted to a pH of 6 to 8 before performing a further treatment.

23. The process according to claim 22, wherein the further treatment comprises addition of NaOH to the flow-through.

24. The process according to claim 6, wherein the unspecific anions are replaced by the specific anion Cl⁻ or OH⁻.

25. The process according to claim 24, wherein if the unspecific anions are replaced by Cl⁻, the pH of the flow-through is adjusted to a pH of 6 to 8 before performing a further treatment.

26. The process according to claim 25, wherein the further treatment comprises addition of NaOH to the flow-through.

27. The process according to claim 7, wherein the pH of the clarified solution is adjusted to a pH in the range of 6 to 8.

28. The process according to claim 11, wherein the purified solution is concentrated by nanofiltration and/or reverse osmosis.

29. The process according to claim 28, wherein the purified solution is concentrated by nanofiltration.

30. The process according to claim 29, wherein a nanofiltration membrane is used which has a molecular weight cut-off in the range of 100 to 200 kDa.

31. The process according to claim 15, wherein the clarified solution and/or purified solution is subjected to discolouring by a treatment with activated charcoal and/or a treatment with a cationic ion exchanger and an anionic ion exchanger which are coupled in series.

32. The process according to claim 31, wherein said discolouring is performed iii) before or after diafiltration and/or concentration of the clarified solution; and/or iv) before or after electrodialysis and/or diafiltration of the clarified solution.

33. The process according to claim 17, wherein the purified solution is subjected to crystallisation by addition of butanol to the purified solution or without addition of any organic solvent to the purified solution.

* * * * *